(12) United States Patent
Habener et al.

(10) Patent No.: US 6,274,310 B1
(45) Date of Patent: Aug. 14, 2001

(54) COMPOSITIONS AND METHODS FOR DETECTING PANCREATIC DISEASE

(75) Inventors: Joel F. Habener, Newton Centre; Doris A. Stoffers, Brookline, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/881,450

(22) Filed: Jun. 24, 1997

(51) Int. Cl.$^7$ .............................. C12Q 1/68; C12P 19/34; C07H 21/04

(52) U.S. Cl. .................. 435/6; 435/6; 435/91.2; 435/91.5; 435/91.51; 536/23.5; 536/24.31; 536/24.33

(58) Field of Search ........................... 435/6, 91.2, 91.51, 435/91.5; 536/24.31, 24.33, 23.5; 935/17, 77, 78

(56) References Cited

U.S. PATENT DOCUMENTS 5,741,673 * 4/1998 Montminy et al. ................ 435/69.1
5,849,989 * 12/1998 Edlund ..................................... 800/2
5,858,973 * 1/1999 Habener ................................ 514/12

OTHER PUBLICATIONS

Inoue, H. et al. Diabetes 45:789–794, Jun. 1996.*
Marshak, S. et al. Proc. Natl. Acad. Sci. USA 93:15057–15062, Dec. 1996.*
Stoffel et al. Genomics 28:125–126, Jul. 1995.*
Catton. Mutation Research 285:125–144, Jan. 1993.*
Chevre et al., 1998, "Insulin Promoter Factor 1 gene is not a major cause of Maturity–Onset Diabetes of the Young in French Caucasians", Diabetes, 47(5): 843–844.
Froguel et al., 1992, *Nature* 356: 162–164.
Jonsson et al., 1994, *Nature* 371:606–609.
Leonard et al., 1993, *Mol. Endocrinol.* 7:1275–1283.
Miller et al., 1994, *EMBO J.* 13:1145–1156.
Offield et al., 1996, *Development* 122:983–995.
Ohlsson, et al., 1993, *EMBO J.*, 12:4251–1993.
Peers et al., 1994, *Mol. Endocrinol.*, 8:1798–1806.
Peshavaria et al., 1994, *Mol. Endocrinol.*, 8:806–816.
Stoffers et al., 1997, *Nature* 15:106–110.
Tattersall et al., 1975, *Diabetes* 24:44–53.

* cited by examiner

*Primary Examiner*—Carla J. Myers
*Assistant Examiner*—Diana Johannsen
(74) *Attorney, Agent, or Firm*—Kathleen M. Williams; Palmer & Dodge LLP

(57) ABSTRACT

Methods for screening a patient for pancreatic disease are disclosed and are based upon detection of a mutation in the gene encoding insulin promoter factor-1 (IPF-1) which is linked to diabetes mellitus and pancreatic agenesis.

82 Claims, 16 Drawing Sheets

```
              Codon
               63
WT:    S  P  |P| D  I  S  P  Y  E  V  P  P  L  A  D
       AGCCCCCCGGACATCTCCCCGTACGAGGTGCCCCCCCTCGCCGAC
Mut:         •R  T  S  P  R  T  R  C  P  P  S  P  T D  P  A  V  A  H  L  H  H  H  L  P  A  Q  L  A  L
       GACCCCGCGGTGGCGCACCTTCACCACCACCTCCCGGCTCAGCTCGCGCTC
       T  P  R  W  R  T  F  T  T  T  S  R  L  S  S  R  S P  H  P  P  A  G  P  F  P  E  G  A  E  P  G  V  L
       CCCCACCCGCCCGCCGGGCCCTTCCCGGAGGGAGCCGAGCCGGGCGTCCTG
       P  T  R  P  P  G  P  S  R  R  E  P  S  R  A  S  W
                                              Codon
                                               122
       E  E  P  N  R  V  Q  L  P  F  P  W  |M| K  S
       GAGGAGCCCAACCGCGTCCAGCTGCCTTTCCCATGGATGAAGTCT
       R  S  P  T  A  S  S  C  L  S  H  G  *
```

FIG. 2A

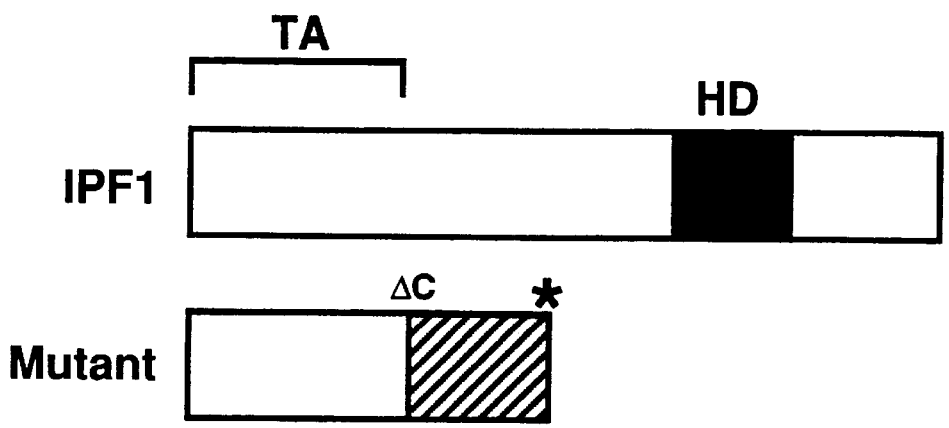

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 400 nucleotides
      (B) TYPE: nucleic acid (C) STRANDEDNESS: double
            (D) TOPOLOGY: linear (ii) MOLECULE TYPE: genomic DNA (ix) FEATURE:
            (A) NAME/KEY: human IPF-1 gene
            (B) LOCATION: exon 1

(xi) SEQUENCE DESCRIPTION: SEQ ID NO: 1:

```
CCAATCCCGG GCCGCAGCCA TGAACGGCGA GGAGCAGTAC TACGCGGCCA CGCAGCTTTA      60

CAAGGACCCA TGCGCGTTCC AGCGAGGCCC GGCGCCGGAG TTCAGCGCCA GCCCCCCTGC     120

GTGCCTGTAC ATGGGCCGCC AGCCCCCGCC GCCGCCGCCG CACCCGTTCC CTGGCGCCCT     180

GGGCGCGCTG GAGCAGGGCA GCCCCCCGGA CATCTCCCCG TACGAGGTGC CCCCCCTCGC     240

CGACGACCCC GCGGTGGCGC ACCTTCACCA CCACCTCCCG GCTCAGCTCG CGCTCCCCCA     300

CCCGCCCGCC GGGCCCTTCC CGGAGGGAGC CGAGCCGGGC GTCCTGGAGG AGCCCAACCG     360

CGTCCAGCTG CCTTTCCCAT GGATGAAGTC TACCAAAGCT                           400
```

(2) INFORMATION FOR SEQ ID NO: 2:

(i) SEQUENCE CHARACTERISTICS:
            (A) LENGTH: 124 amino acids
            (B) TYPE: amino acid
            (C) STRANDEDNESS: single
            (D) TOPOLOGY: unknown (ii) MOLECULE TYPE: protein (ix) FEATURE:
            (A) NAME/KEY: human IPF-1 protein
            (B) LOCATION: amino acids 1 through 124

(xi) SEQUENCE DESCRIPTION: SEQ ID NO: 2:

```
Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro Pro His
        35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser
        115                 120
```

(2) INFORMATION FOR SEQ ID NO: 3:

(i) SEQUENCE CHARACTERISTICS:
            (A) LENGTH: 59 amino acids
            (B) TYPE: amino acid
            (C) STRANDEDNESS: single
            (D) TOPOLOGY: unknown (ii) MOLECULE TYPE: protein (xi) SEQUENCE DESCRIPTION: SEQ ID NO: 3:

```
Arg Thr Ser Pro Arg Thr Arg Cys Pro Pro Ser Pro Thr Thr Pro Arg
1               5                   10                  15

Trp Arg Thr Phe Thr Thr Thr Ser Arg Leu Ser Ser Arg Ser Pro Thr
                20                  25                  30

Arg Pro Pro Gly Pro Ser Arg Arg Glu Pro Ser Arg Ala Ser Trp Arg
                35                  40                  45

Ser Pro Thr Ala Ser Ser Cys Leu Ser His Gly
    50                  55
```

(2) INFORMATION FOR SEQ ID NO: 4:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer PCR4

(xi) SEQUENCE DESCRIPTION: SEQ ID NO: 4:

```
GGAATTCGGC TGTGGTTCCC TCT                                          23
```

(2) INFORMATION FOR SEQ ID NO: 5:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer S16

(xi) SEQUENCE DESCRIPTION: SEQ ID NO: 5:

```
CAGAGAGAAG GCTCCTG                                                 17
```

(2) INFORMATION FOR SEQ ID NO: 6:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer S17b (xi) SEQUENCE DESCRIPTION: SEQ ID NO: 6:

```
AGCGAGCAGG GGAGGCG                                                 17
```

(2) INFORMATION FOR SEQ ID NO: 7:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer S18

(xi) SEQUENCE DESCRIPTION: SEQ ID NO: 7:

GGGACGCTTG GAGGTAA                                                              17

(2) INFORMATION FOR SEQ ID NO: 8:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer PCR2

(xi) SEQUENCE DESCRIPTION: SEQ ID NO: 8:

CGGGATCCGC CGAGCTTCTT GTC                                                       23

(2) INFORMATION FOR SEQ ID NO: 9:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer PCR3

(xi) SEQUENCE DESCRIPTION: SEQ ID NO: 9:

GGATTCTGGG GCTTGGTGGC TC                                                        22

(2) INFORMATION FOR SEQ ID NO: 10:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer S1

(xi) SEQUENCE DESCRIPTION: SEQ ID NO: 10:

CGCCTACGCT GCGGAGC                                                              17

(2) INFORMATION FOR SEQ ID NO: 11:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer S14

(xi) SEQUENCE DESCRIPTION: SEQ ID NO: 11:

AGAAGCTCCT CGCCGGAG                                                             18

(2) INFORMATION FOR SEQ ID NO: 12:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer S12

(xi) SEQUENCE DESCRIPTION: SEQ ID NO: 12:

AGGAGGAGGA CAAGAAGC                                                     18

(2) INFORMATION FOR SEQ ID NO: 13:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: primer PCR7

(xi) SEQUENCE DESCRIPTION: SEQ ID NO: 13:

CGGATCCTAG GGCCTCTGCT CC                                                22

(2) INFORMATION FOR SEQ ID NO: 14:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: other nucleic acid (ix) FEATURE:
        (D) OTHER INFORMATION: Wild-type primer for allele-specific
            hybridization of IPF-1 gene.

(xi) SEQUENCE DESCRIPTION: SEQ ID NO: 14:

ATGTCCGGGG GGCTGCC                                                      17

(2) INFORMATION FOR SEQ ID NO: 15:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (ii) MOLECULE TYPE: other nucleic acid (ix) FEATURE:
        (D) OTHER INFORMATION: Mutant primer for allele-specific
            hybridization analysis of IPF-1 gene.

(xi) SEQUENCE DESCRIPTION: SEQ ID NO: 15:

CAGGGCAGCC CCCGGAC                                                      17

(2) INFORMATION FOR SEQ ID NO: 16:

(i) SEQUENCE CHARACTERISTICS:
        (A) LENGTH:  45 amino acids
        (B) TYPE:  amino acid
        (D) TOPOLOGY:  unknown (ii) MOLECULE TYPE: protein (xi) SEQUENCE DESCRIPTION: SEQ ID NO: 16:

Met Arg Val Pro Ala Arg Pro Gly Ala Gly Val Gln Arg Gln Pro Pro
1               5                   10                  15

Cys Val Pro Val His Gly Pro Pro Ala Pro Ala Ala Ala Ala Ala Pro
                20                  25                  30

Val Pro Trp Arg Pro Gly Arg Ala Gly Ala Gly Gln Pro
            35                  40                  45

(2) INFORMATION FOR SEQ ID NO: 17:

(i) SEQUENCE CHARACTERISTICS:
        (A) LENGTH: 32 nucleotides
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: INS-FLAT element.

(xi) SEQUENCE DESCRIPTION: SEQ ID NO: 17:

GATCCTTCTT AATCTAATTA CCCTAGGTCT AA                                    32

(2) INFORMATION FOR SEQ ID NO: 18:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: SMS-TAAT1 element (xi) SEQUENCE DESCRIPTION: SEQ ID NO: 18:

GATCCCTGAT TGCATATTAA TTCTCAGATA                                       30

(2) INFORMATION FOR SEQ ID NO: 19:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: SMS-TAAT2 element (xi) SEQUENCE DESCRIPTION: SEQ ID NO: 19:

GATCCGATCT CAGTAATTAA TCATGCACCA                                       30

(2) INFORMATION FOR SEQ ID NO: 20:

(i) SEQUENCE CHARACTERISTICS:
        (A) LENGTH: 37 nucleotides
        (B) TYPE: nucleic acid
        (C) STRANDEDNESS: double
        (D) TOPOLOGY: linear (ii) MOLECULE TYPE: genomic DNA

```
    (ix) FEATURE:
         (A) NAME/KEY: SMS-UE-B element (xi) SEQUENCE DESCRIPTION: SEQ ID NO: 20:

GATCCGCGAG GCTAATGGTG CGTAAAAGCA CTGGTGA                                37

(2) INFORMATION FOR SEQ ID NO: 21:

(i) SEQUENCE CHARACTERISTICS:
         (A) LENGTH: 24 nucleotides
         (B) TYPE:   nucleic acid
         (C) STRANDEDNESS: double
         (D) TOPOLOGY:  linear (ii) MOLECULE TYPE: genomic DNA (ix) FEATURE:
         (A) NAME/KEY: SMS-PS element (xi) SEQUENCE DESCRIPTION: SEQ ID NO: 21:

GATCCAGGCA AGATTATTTG GTCA                                              24

(2) INFORMATION FOR SEQ ID NO: 22:

(i) SEQUENCE CHARACTERISTICS:
         (A) LENGTH:  4853 nucleotides
         (B) TYPE:   nucleic acid
         (C) STRANDEDNESS: double
         (D) TOPOLOGY:  linear (ii) MOLECULE TYPE: genomic DNA (ix) FEATURE:
         (A) NAME/KEY: IPF1 gene, contig 1.

(xi) SEQUENCE DESCRIPTION: SEQ ID NO: 22:

TCACTGCCAC CCCCNNGTGN TTACTTNGNA CTCCTCAACT AATTGAACAT TTCTGTAAAT          60

TGGNCTCCAT TTCGATGCTN CATTTGCTNC CATTTANTAT TTGGGCTCGG CCCTNNAGAA        120

AGAAAAGAGG NTCTCAGAAG AAAGCAACTC CGCCGGGTGG GGGCGCCGAA AAAACCCCGG        180

CTACCCNCNG TTGGGGGGGA GGAGGAGGGG ATCGCCGGGG GTATCCCATG GNGGCGNNNT        240

CTCACTAACA CAATTAGTAT TTTCTGCTGC CTGCGACCTA TAGAGGGGCC CCAGGGAGCA        300

AAGSTCANNC AMCCATTTNT TATTGTTATT ATTATTATNA GATNAAACAA WGTTATCTGG        360

AATTTTATCA CGTACAGCCG TATAAAAAAC GCATCAAGCG GAACCCTCCG CTTAGTAAGG        420

TCGTGTGTTG TACTTCCCCG TGGATCTAGC TCCTGGTATC GTAAAATCGC CGAGTCCATT        480

ACAGGCGAAA TGCGTTTCCG CTCTGAATCC CCGCTGACGC CTGCGCCCCC TCCAAGCCGC        540

CTCGCCCACA ACAGGCCCGG CAGCGATACC GAGCCATTAG GCGAGCACCT TCCCGAGCCA        600

TTTAACAGCA GCTCTTATGG ATAAATAAAC AAAAAAGGCT GTAAACCAAT TAAAGTGTGG        660

ACAGTGAAAA AGTCGTTTAT TAGCTGGACG TCCTGATAGT CCTCGCTGAT ACTGGAGGTC        720

CTTGCCGGCC CTCTTCCCCC TTTCCCTTCA CAGAGACGCG GTTTACACCC GGGAGAACAC        780

AGGTTACCTT GTTCTTGGTA AGTGGCTAAG TCTTCCTCGG TGGTTTCAGA GGCATGCTAA        840

GGGCTGAATT TGGCTTGGTG ATAGGATTTT TAAGCCACTG CATCCCATTA TAAATGAAAA        900

AAACAGATGA ATCCCACTTA ACTCCAAGGT ATACATCATG AATGCACGTG GAATTTATAT        960

TCATTTTATA ATTAAATCTC TGTTGAAAAT AAAAATTGTT TCTTGAGTTG GAAAATTCTG       1020

TAAAGCAAAC GATGTGATGT GTGGAATGAG AATACTTCTA TAATTGATTG CACTTTAGTT       1080

CATTAGCATT TCCTTCAATG AGCACTAATG CAGGCAGGTT TTCATTTTCC TAAGTCGAAT       1140
```

```
CAATGTTTCC CTCCTGCTGG TTTATGAATA CCCAGAATTG GCCGAGGGCG KKGGCTCACG   1200

CCTGTAATCC CAGCACTTTG GGAGGCTGAG ACAGGCGGAT CATGAGGTCA GNGAKWTCGA   1260

GACCATCCTG GCTAACATGA TGAAACCCCG TCTCTACTAA ACCTACAAAA AAATTTAGCC   1320

GGGCGTGGTG GCGGGCGCCT GTAGTTCCAG CTACTTGGGA GGCTGAGGAA GGAGAATGGC   1380

GTGAACCCAG GAGGCGGAGC TTGCAGTGAT CCGAGATCGC GCCACTGCCC TCCAGCCTNG   1440

GAGACAGAGC GAGGCTCCGT CTCAAAAAAT TAAAAATATA TATATATATA TAAATAAATA   1500

CCCAGAATTT GGTATCCAGG TCTGAGAGGG GCCAGGGAAA CCCAGCTTGG GTTGTGGGGA   1560

TTGGAGAGAG GAAAGGACCT CAGACTTTGA ATGAANGGTT TTCCAATATT CCTAGGGCTA   1620

AGCAATCTAG TGAAAATAAG CAGAGAGCTG AAATTATTTT CCAGATGATT CAGTGATCCC   1680

TGAACTGTAA AGATAAAAGC AGCTTAAAAA CCGAATTGAA TTGGGTAATT GTCTTATTCC   1740

CTACCTTGTT AGCTCTCTCT GGTGTAAGAG GAGTAGAAGG GCAGGAGGGG GGACTCTGTG   1800

TGCCCCAGAA CTGTCTGCTG CTTCCTCCAG CCACTGCTCA ACGCTTCCTC CCTGGGAGTG   1860

GGGCCCCCAG ACACGAGCTC TTTCCACTTT TGGTTTAATC CTTCCGTGGT CCTCAGTTCA   1920

CTCTGCTGAT GAAAGGAAAA GTATGAAAGG ACTTTCAGGC TCCAAANGAT CTGAGGTCAN   1980

CTGTTGCYCC CCACTCCTGG TGTTCCCGGT GGCTCACCCC CTACAGCTCT GGACTCACCC   2040

CTTTGGTTGT CTCATCTCTG GTTCTACCTT CCAGATGTGC AGTCTCCAGA AATCCCTGCT   2100

GCTTCCCTTC TGAGCTTAGT CCTAGGTAAC CAGCTCCTTG CTTCCACACA GTTCCTTTTC   2160

TTTGCCTTCC ACCTCCTCCT CCCACCACCA TTTCCTATGA CTAATCCTTT GTTCTCCTAG   2220

GAGCCTCTCC TTACCTCCAG GTTCCTGCTG CAGCCTAAAG AAGGCTTGAC CCACACTACC   2280

CTCCAGCTTC CTTCCTCAAC CATCCTACAT TTCACATGGT TTATGCTTTG AAGGACCCAG   2340

ATTTTCGGTA ACATATACTG ATCAAATGCC TGTAGATCTC TCACTGTGCA CCTGCCTGCA   2400

CACTCTTTGA GTAACCAAAA CTCATTGGTA GAAATATGCG CTGGCTTTGG CGGGCCATAG   2460

AAAGGTCAGG AGCTGCATAC ACCTGTCCTC CACATCAGGC TCTGCCCTGC ACAAGCTGTG   2520

TGTCCCTTGC CAAGTTACAT GACTTCACTA AGCTTCCCTG CCCTTATTTG TAAAATGGAA   2580

ATACTAGCAC TGTTCCATAA GCTGGCCCCG TTGCACATAG TAATCGTAAT GGCAAATGCA   2640

TGGAGCCAGG CGTTGTTTAA ATATTTTCCA ATGTTAACCC CATGAGCCAA TTACTGTTAT   2700

CCCATTTTCC AGTGGAGGAA ATTGAGGCCC AGTGATGGTA AGTTACTTGC CTAGAATTAT   2760

ATAGCTAGTA AGTGGCAGAG CCTAGATCCA AGCNGAGATG AKGTGGCTTT TTTKTTKTTK   2820

TTKTCSAGAY AGAGTYTYRC TCTGTNGCCN ANGCNNGNGT GCNNTGGCNY NANCTNGGCT   2880

YACNGCAACC TCCACCTSCT GGGTTCAAGC GATNCTCCAG CCTCAGMCTC CCAAGTAGCT   2940

GGGATTACAG ACAYNTGCCA CCATGCCTGG CTAATTTTGT ATTTTAGTA GAGACGGGTT    3000

TCACCATGTT GGTCAGGCTG GTCTCGAACT CCTGACCTCA GACTATCCAC CCACCTTGGC   3060

CTCCCAAAGT ACTGGGATTA CAGGCCACCA TGCCTGGTTT TTTGTTTTTT GTTTTTTTT    3120

TTTGAGACTG AGTCTTGCTC TGTCGCCTAG GCTGGAGTGC AGTGGCATGA TCTCGGCTCA   3180

CCGCAACCTC TGCCTCTGGG GTTCAAGCGA TTCTCCTGCC TTAGCCTCTC TAGTAGCTGG   3240

GATTACAGGC ACGCACCACC ATGCCCGGCT AATTTTTGTA TTGTTAGTAG AGACAGGGTT   3300

TTTCCTGTTG GCCAGGCTGG TCTCGAAGTC CTGACTTCAA GTTATCTGCC CACCTCGGCC   3360

TCCCAAAGTG CTGGGATTAC AAGCATGAGC CACCACACCT GGCNTTGATG TGGCCTTAAA   3420

ATCCATTCTG TTGGCTGTGA CACTGTACTA TCTTACTATA TAGTAGGCAC TCAAAAAATA   3480

TTTTTTATTG TTTTTGTGAG GATTTAATGA GACAAAACAT CTAATGTTTT TGGCACTTTG   3540
```

```
AAAGCATTCA ATAAATGGTC ATCTCTTCCT TTCTCCCCCA GCATTGCTTT TAATGTGCAT      3600

ATAAACATTG AACTATTGGC TATTACTGCA TCCAGAAGAA TGACAGACTA TCACCATGAG      3660

CTGATGTCTA AAGATATTTC CAGATGGGTA GACCTGGAAA GGTATATTCA GGAACACTGG      3720

GAGGAAGTAC TTAGTAGGTA TATTACTCAG TGTTTTAGGG GAATGTGCCC CCAGGTACAG      3780

TCCTGCTTAA AAGGGCTGGA GGAGGTGGAT TGCTGGAGAA CTCTCATGTC CGCCATCAGC      3840

ACACCACAGA GAGACCCCAC AGGTGTGGAG AAGGGGCAGG GCCTTCTTTT TCACAGCCAG      3900

GAAAGCCAAA ATAAGACTT GAGCAGGTGA ACTAATCACA ACTCAAAATG CCTTAGCTAT      3960

CCCAGTAGGT GTGGAACCCA GCATCTAAGT AGTGTGTTCT GGCCAGAGAG CACCCCNACT      4020

AGCATTGTCT GTGGTTCTTG CTTTCGTGGG TTGGAGATGA AGCTGTCATC ATAAACTCAG      4080

AGGAAACCTT AAAATGTCTA GGGAGGGAAA GGAGTCATTC TAGTCTCTAG GCCAGAGCAG      4140

AGCTGGAATC CTGCCCCATT CCTGCTTTTT CCACATCAGA AAAACGGTCA TGGTCAACCC      4200

TGGKTGTCTT TGTGAGGNTG CAGGANCACT GCCGTCAAAG TGATTCCTCT GTGTGTCCCC      4260

CCAAATCAAA TCCACGTTAA AATTAGAAAT CGATGGGGTT AAGATGGGAG AGTCAATGCT      4320

AAACTCAGAG CAGCACAAGT GAAGCCTTCT CTTTTGACAG CCTAGGCTAG GTCCACAGCC      4380

TCTCTTGCAA AGATTAAAGT AAAAGGCTAA CTGACTGTGG TCTCAACTTT ATCATATTTG      4440

CCAATTAGGA ATTCTTCCTG TGGTAGATAT CTCTTAGGAG TGTATTGTTG TGAACAGAGA      4500

CACAGTATTT GGATACATYT ATTWTWKAWA TWTTCTCCAG YKACAYATTK CAMCACATNT      4560

ACCYYCRGGC RMATCTCAGA RANAWACAMA CTCTTWCTNM TCMATGRAGT AACATGGAKW      4620

TANAGGGRNG TGTTCCYGGR RGTGTGACTC TGWRCTGTGT ATATCAAGAR KCWCTGGGAT      4680

GCTTATAAAA TGARAATATC TGAGMCCMMC CCCAGACCYY CTGWATAACG AYATGGGGGT      4740

GAGTGAGACT GGGGAGTCTC CATTTTAAAC ATGTACACAG TCATTCTCTA NTTTGTTTTT      4800

TTTTTGCTGC TGTTGNTGAG ACAAAGTCTC ACTCTGCTGC CTAAGCTGGG GTG            4853

(2) INFORMATION FOR SEQ ID NO: 23:

(i) SEQUENCE CHARACTERISTICS:
        (A) LENGTH: 5658 nucleotides
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: IPF1 gene; contig 2.

(ix) FEATURE:
        (A) NAME/KEY: transcriptional start
        (B) LOCATION: nucleotide 2002

(ix) FEATURE:
        (A) NAME/KEY: translational start codon
        (B) LOCATION: nucleotides 2106 through 2108

(ix) FEATURE:
        (A) NAME/KEY: first coding region
        (B) LOCATION: nucleotides 2106 through 2511

(ix) FEATURE:
        (A) NAME/KEY: intron 1
        (B) LOCATION: nucleotides 2512 through 5858

(xi) SEQUENCE DESCRIPTION: SEQ ID NO: 23:

GCGGCCGCAG ACAATGGACT CATTGACGCG GGCGCACAGA GATTAGGTGC CCGGGCCCCA        60
```

-continued

```
CGGCCTTTCA CTCTCTGCCC CCACCAAAAC TGCAGGTGGC ACTTTTCCCT GAAGAAATCA    120

CCGAAACTCT CCCCGCCCGC CGCCGTGCTT CCCTTGGCCT GTCTTCGGTG ACAGCAAGGG    180

CATCTACAAG CCAGGGAGCC ACACATCAGA GCCACACACA TGAGGCCACA GGCCAGGAAG    240

CCACACACAT GAGTTCTCAC ACATCGAAGC AAATGCTGAG ACTATACCGG CCTCCCGCAA    300

GAGAAGGAAT CTGCAGAGAA GTCCACATTC CCGACTGGCT TTTTTGTCTT TTAATAAAAA    360

TAAAGAGTCC TCAGAATAGA GCACTCAATC CGCACTTAAA ACACAAATAT TTCCAGTAGG    420

AAGAAAGAAA TACATTAAGA TTGACTCTCA AAGGTCTGGA TGTTGGTGCG TTGTTTAGGA    480

AAGGCGGAGC AGTGATTTTT CTCTGGCTTG GTTCTTTGTG GTTCAAGCTC TCTCTTGCTG    540

AGACGTTTCT GCAAAGCTGT CTAGTTTTTC TAAAACCCAC GGTGGCGTTT CGAGAAACGT    600

CCTCATTTCG GGAGTATCCA GTCAGAGGCT GGTCAGGCCG CCAGGCCTAG CGGATCATGC    660

CCAGGCAGGG GGTTGGACGT CACCGCCACC CGGAGGTCAT CCATCCGCGT CAGTGGGTGC    720

AGAAAAAGTG GCCCTGTTTA AGTCAGGACC CCAGAATGCC CAGAAGTTAC TGAATGGTTT    780

GAAGCCAAGC ACAGATGTTA TCATGGAAAA TGCAGCGTTT TTATTTCTTT TTCTAAATAT    840

GTAACTCTTC CTCCACTTCC CCCTCTCCTG CTTGCCTTAT TTCAATTGCA AGCAGAAGAG    900

AGTGAGTGTT CTCTGCCGGC AAACTCCGCC AGGGTCCCGG CCCGTAGAGA GTCGTCAAGG    960

GTCTGGAACC CCCGTGCCAA CACCTGCCCC TGCTTCGCAG CCCCAAGAGG AAGGCCGCGT   1020

CTTTCCCCCT CGCTGTATTG GAAGCTACG TTCCGGGCTG GCCAAATGGG CCCCAATTTT    1080

CCAAAACCCA AATTTGTAAT ACCCTTCAAT TTTTTAAAAA AAAGAATTTA AAAAAGTCTC   1140

TGTGAATGCT TCAGAAGTTA CCGTTTACAC CCCAGAAGTA CTTGCAGCAC ATCCACAAGT   1200

AAAAACACAC AACGAATGCC AGAGTTTCGT GTGTTTTTA ACCGACATCT TTGTGGCTGT    1260

GAACAAACTT CATAAATAAA ATAGAATCAA ATGCTTCTGA CCTAGAGAGC TGGGTCTGCA   1320

AACTTTTTTT TTATCGTATT CCGCAACAGT TAAATAAAAA ATTAAAAACT CAACATGTCT   1380

CCTTGTAAAC TACATCAATT AACAAACACA CTATGTCCAT TATCAAATAT AATAGAAAAA   1440

ATATAGGAAA ATAGAAAATA GAAAAATATA GGAAAATAGA AACTTTTAAG CCACGGTGAA   1500

AATGTTTCTA TAAATGAGTG GTTCTAATGT TTTCGTGAGC GCCCATTTTG GGGAGCACCG   1560

CCAGCTGCCC GTTCAGGAGT GTGCAGCAAA CTCAGCTGAG AGAGAAAATT GGAACAAAAG   1620

CAGATGCTCG CGGGTACCTG GGCCTAGCCT CTTAGTGCGG CCAGCCAGGC AATCAACGG    1680

CCCCCGCTGA ACCACGTTTG GGCCCGCCTN GGGAGNCTTG GTNNNNNNNN NNNNNNNNNN   1740

NNCCGNGNTG GCTGTGGGTT CCCTCTGAGA TCAGTGNGGA GCTGTCAAAG CGAGCAGGGG   1800

TGGCGCCGGG AGTGGGAACG CCACACAGTG CCAAATCCCC GGCTCCAGCT CCCGACTCCC   1860

GGCTCCCGGC TCCCGGCTCC CGGTGCCCAA TCCCGGGCCG CAGCCATGAA CGGCGAGGAG   1920

CAGTACTACG CGGCCACGCA GCTTTACAAG GACCCATGCG CGTTCCAGCG AGGCCCGGCG   1980

CCGGAGTTCA GCGCCAGCCC CCTGCGTGC CTGTACATGG GCCGCCAGCC CCCGCCGCCG    2040

CCGCCGCACC CGTTCCCTGG CGCCCTGGGC GCGCTGGAGC AGGGCAGCCC CCCGGACATC   2100

TCCCCGTACG AGGTGCCCCC CCTCGCCGAC GACCCCGCGG TGGCGCACCT TCACCACCAC   2160

CTCCGGCTC AGCTCGCGCT CCCCCACCCG CCCGCCGGGC CCTTCCCGGA GGGAGCCGAG    2220

CCGGGCGTCC TGGAGGAGCC CAACCGCGTC CAGCTGCCTT TCCCATGGAT GAAGTCTACC   2280

AAAGCTCACG CGTGGAAAGG CCAGTGGGCA GGTAAGCCTG GCTCCCCACC CCTTTCTCCT   2340

TTCCGGTTCT CACCCGGNNG CCTTACCTCC AAGCGcTCCC AGGAGCCTTC TCTCTGTTCC   2400

CGGCGCCTTG GATTATCCCG GGTCGGACTA AACTACATCA GGGAGCTACC GAGCCCATCC   2460
```

```
CTCACAGCAG TGCTTCTCTA GTCCAGTTTG AAGCATCTTT CCCACCCAGC TCTCCTGGGA    2520

GTGTACACTC CTTCCTTCCC TGTTCGCTGA GCCCATCTTC GCCCCAGGAG CCCGCGCTCC    2580

CAGCGCCATC CTTAGAGAGC CGAGGCTGAG TCCTGCTCAG GGCTTCGGAC ACTACAGATC    2640

CTCCTCCAGC AGGGGATCCG GGAACCCAGG ACTCCTTGGT AGTGCACATC GAGGAAGCCG    2700

AGTAAGGACA TGGGTGCCTC GGACCCAGGC CCCAGATCGC CTTCGGAGCC CCGGAGCCCC    2760

TCACTTCCCG CGCTTCGTTA AGGAAGGGCA GGCATCTARG GGCGCCASGT AGGTGCAGAA    2820

AGGCAGGGAG GGAAAGGAAA CTGCACCCAA CCCAGCAGTG TCCGGCTGCC CTGGTTGTGG    2880

AAACAGGATA GATAAAGAGG AAGGGGCTGG GGCAAGGCGG GGGCTCACCG CGAGGCTGAA    2940

AGCCGGCCTC TCAACNTCAG AGCCTGGCAG CTAGGAGAGC AATCTGAGAA GCGAATTCGT    3000

TTTTCACCAA CCGAAAGCAA TTGAAGCTGT CTCCCCGCAC CGCTTCCCAG GAAGTAATTT    3060

TTCAGGAGAT GGGCGCTCCC TGCCTAACTG GTGGGGAAGC GAAAAGCCTG NTTCCTGCGG    3120

CCCTCCGCGC CGGCANAAAA CAGAANGTCT TTCCCGGAAC CGGGARCCGG ARGCACGGGG    3180

TANCCCCCGG GTCCTTTGCG GCCCCNCGCG AGCGGCAANT TCCGGCGCGG CCTGTGTCGT    3240

CGCCGCTACT CACTGTCATC GCTGCCGTGC CTCAGCCACT TCTGGTCACA CCTGCACCGC    3300

AAATAGTTGC CTTTTCCTTT CAACTGGCAG CCGGGAGTAG GGGGAAGCAG CTCGAGCCGG    3360

CGTCCCCCGG CCCACCCCGA AAATCCTCAG CGCCCATCTG CGGGGTCTGG CCAGCCCTGC    3420

CTGACACTGA CCCCAGGCGC AGCCAGNAGG GGCTTTGTGC GGGANANGGA AGGGGAACCC    3480

ATCTTTNNTN NGGTCCACGG GACTCTCTTC TTCCTAGTTC ACTTTCTTGC TAAGGCGAAA    3540

GTCCTGAAGC AGGACAAAGG CTGAACTGCG CTGCAATCGT CCCACCTCCA NCGAAACCAA    3600

GTTGACAGGG GCGCCCCAAG CTGCCACGGC GCCTCTGCAA ATTTATCCAG CTCGCGCAGC    3660

CCGGGCCAAA GGCCTTGAAG TCTCCGGAAA TGCGGGGTTC TTAGGAGGCG GGAGGACAGT    3720

CCCTCGAACA AGGTGGGGG GCTCCTCGTC CTCACCCAGT TTTCTTCCAG GGCTGCCTCC    3780

CCTCCAAACC TCTCTTCTGG CCTCCTAGGC CCTSGGAGCT CCTGCTTTCC CACCYTGGGC    3840

CTTCYTCAGG AAATGGGMGA CATCAGGGTC CCGAAAGAGG ATTTGTGAGG TGGAGTAACT    3900

TCCYTATCCC AACCCAAGGG GTGATACMTM TGMTMTGKAK GAYTTKGGCT TAGGCTGACC    3960

CAAGAAGCCA GAAAGTAAAA CCAGAAGGCA AATCAGCAGC CTTGGCGAGG GTTCGGGGAC    4020

CCAAGGAGGG CGACACTCTC GGGCTGGAGT TGGCCCCAGG CCTTTGCTGG CGCCCTCTAA    4080

CCCGCTGCAT GCTCGACTTT CGGGGAAGGA GACGACCTCC CCTCTCTTCC CCTGGAAGCC    4140

GTCTGCGGGG CCGGCTGCTA TCCCCGCGTT CCTTTAGGGG AAACTTCGAT GGAGCCGAAA    4200

TTCAAAAATT GCAAACCCAC CTGCCCCTGG GAAGAGCGAA GTGACAAAAG GGCTCTCMAY    4260

GGNCAGTACG AATTTGAATG TTAATGACAA CAGAGGTTTT GAAAAACATT GACCCCCAAA    4320

TGCTTCAGCA GCGCTGTCCA GNTGGCACNT AAANTGCATC ANTNTGCGCC TTGGGGAAGG    4380

GCCCAGGCTT GGNGACATNG ACATTTTCCC ACCATCCTCA ACCTCCACCC CTGCCGCGTC    4440

GCGCTGAGCA CAGGTCCCCC GGGAATAGTG CACCCCAGGA AGTCTCTCCC TGAGCAGTCT    4500

CTCGCAGGGA CTTCACGAAG CCCTCTCGCA GGGACTATAC GAAGCCCGCA GCCTAAGGCA    4560

GGAACCCAGA GACATGTCGG TTTAATGTAA AAACTTTGGA GAGCCTTTCA AAATGTTTAT    4620

TGAAGGCCCG TCTCGCTTCT CTCCCAGGCG TGGGATGCCA GGTAGATTCG GGGATGCCCC    4680

CAGGGAGTAG AACTCTCCCT GGACTAGGGT TTGAGCCTCT GCTTCAGCTT NTGGCGCCTC    4740

TTCTCGACCT TGGGGGAAA CCCAGTCAGG TTCTCTCGGG AAATTAACCC CGCCCCCAAA    4800
```

| ACACACACAT | TCGCCTTTCA | ATTCGTTAAG | GCTNAGCCAA | CATTCACAGG | AGAAATGTCC | 4860 |
| CCTGCCTTTG | CTGTAAGACA | AGCCTCTCCC | CGGAACTTTG | GTGGAACTTC | CCGCGCCAGC | 4920 |
| GTCCACAGCC | TGGGTGCAGT | CAGTATTTTC | CACAGAAAAG | AAAAGATTGG | GACTTGGCTG | 4980 |
| AGCGCAGCGG | CAAACAGTGA | ATGTGGGTCT | CCAACTTCNT | GGGNCAGGGG | TCCNGTTGCC | 5040 |
| TCTTGGAGAC | ANGAGAGGCT | TGTTTGTGCA | CCATACCACC | TCNTCCGTAG | GGCTGTNGGT | 5100 |
| TNTGCAGGTG | GGTAAGGGCC | CANGTGTCTT | CCCCTCAACA | CCTCTGAGGG | CATTTGGGAT | 5160 |
| CCCAGRGCGT | AGATTCNGGA | GCTGCCAGAG | TTNTGCCTTG | GCCAACGGAC | CCCCAGAACA | 5220 |
| ATATTCTTTC | ANTTTNGCGG | GCAGAAGTCC | GGCTGAAGTT | AAAACAATTA | TGGAGAATTT | 5280 |
| GCTGGTCTCA | GGTTGGGACT | AATTACGATA | TAACTATAGA | GAGAGGAAAC | ACATGGTCAG | 5340 |
| ATATAACAAA | ATGTGTCACA | GTCTCCATTA | GCACAAAGAT | TTTCAAACTG | CAGGTTGCAC | 5400 |
| CCATTCGCAG | GTCATAAAAT | CAATTTACTA | GGTTGAGATT | AGTATTTTTT | AAACGAAATA | 5460 |
| GCAGATAATG | GAGAGAAAAG | TAGATAGCAT | CATACGTGGT | AAACGTTTGT | TTTATGTCCT | 5520 |
| TAAGATTTGT | CAGTATAACT | GACCTGCAGT | GTCCGTGTGT | GAACTACACA | ACGATCCGAA | 5580 |
| ATGTATTTCT | CACATTTGTG | GGTCACCATC | AGGAGGTTTT | TTTTAGCCCT | GGATTAAAGG | 5640 |
| CGTTGNCTTG | CCTTTGTA | | | | | 5658 |

(2) INFORMATION FOR SEQ ID NO: 24:

(i) SEQUENCE CHARACTERISTICS:
        (A) LENGTH: 874 nucleotides
        (B) TYPE: nucleic acid
        (C) STRANDEDNESS: double
        (D) TOPOLOGY: linear (ii) MOLECULE TYPE: genomic DNA (ix) FEATURE:
        (A) NAME/KEY: IPF-1 gene, contig 3.

(ix) FEATURE:
        (A) NAME/KEY: intron sequences
        (B) LOCATION: nucleotides 1 through 359

(ix) FEATURE:
        (A) NAME/KEY: second exon
        (B) LOCATION: nucleotides 360 through 874

(ix) FEATURE:
        (A) NAME/KEY: second coding region
        (B) LOCATION: nucleotides 360 through 802

(ix) FEATURE:
        (A) NAME/KEY: stop codon
        (B) LOCATION: nucleotides 803 through 805

(xi) SEQUENCE DESCRIPTION: SEQ ID NO: 24:

| GGATCCAGCC | GGTTTAACTA | TTATATACAT | TTAAATCAAC | ATCAATCAGC | TGATTAACAC | 60 |
| CGATTATATG | AACGCATTCA | AGGACCACTC | ATTGGCAGAG | CCAAGCTTAG | GCTCACGGCG | 120 |
| AGAGCTGACT | CGAGTTTGGT | CTCCAATAAA | AAGGCTATCT | TTATTAGGAA | GGGCTTGAGT | 180 |
| TACTAGGGAA | GAGCTTCGCG | CGCCTACACT | AGGCGCTGAA | ATGGGATGCT | GGGGCTTGGT | 240 |
| GGCTCCGCGG | AGCAGCTGGT | AGGCTAGGCT | CCCTGGGCCC | CCCTTGAAGG | GTTTGGGCTG | 300 |
| CGTGGGTGGG | GGCTGTGCGG | GGCTCCGGGG | GCCACACTCA | CGCCCTGTGT | CGCCCGCAGG | 360 |
| CGGCGCCTAC | GCTGCGGAGC | CGGAGGAGAA | CAAGCGGACG | CGCACGGCCT | ACACGCGCGC | 420 |
| ACAGCTGCTA | GAGCTGGAGA | AGGAGTTCCT | ATTCAACAAG | TACATCTCAC | GGCCGCGCCG | 480 |
| GGTGGAGCTG | GCTGTCATGT | TGAACTTGAC | CGAGAGACAC | ATCAAGATCT | GGTTCCAAAA | 540 |

-continued

```
CCGCCGCATG AAGTGGAAAA AGGAGGAGGA CAAGAAGCGC GGCGGCGGGA CAGCTGTCGG      600

GGGTGGCGGG GTCGCGGAGC CTGAGCAGGA CTGCGCCGTG ACCTCCGGCG AGGAGCTTCT      660

GGCGCTGCCG CCGCCGCCGC CCCCCGGAGG TGCTGTGCCG CCCGCTGCCC CCGTTGCCGC      720

CCGAGAGGGC CGCCTGCCGC CTGGCCTTAG CGCGTCGCCA CAGCCCTCCA GCGTCGCGCC      780

TCGGCGGCCG CAGGAACCTC GATGAGAGGC AGGAGCTGCT CCTGGCTGAG GGGCTTCAAC      840

CACTCGCCGA GGAGGAGCAG AGGGCCTAGG AGGA                                  874
```

COMPOSITIONS AND METHODS FOR DETECTING PANCREATIC DISEASE

FIELD OF THE INVENTION

The invention relates to the fields of clinical diagnosis and of screening for risk of genetically-determined disorders relating to pancreatic disease.

BACKGROUND OF THE INVENTION

Pancreatic disorders, particularly diabetes mellitus, constitute a major public health problem, as they affect a sizeable proportion of the population and have a profound negative impact on the overall health and quality of life of those individuals so afflicted. While a variety of pharmaceutical compositions have been developed to compensate for reductions in insulin production brought about by pancreatic deficiency, modifications in lifestyle, such as exercise, adherence to a sensible diet, avoidance of tobacco and moderation of alcohol consumption, can do much to alleviate its effects; therefore, it is desirable to conduct genetic screening to identify individuals who are predisposed toward the development of diabetes and other pancreatic disorders while they are still asymptomatic.

Maturity onset (type II) diabetes mellitus is a highly prevalent disease caused by an imbalance between insulin production by the endocrine pancreatic β-cells and the insulin requirements of peripheral tissues. This results in hyperglycemia and secondary cardiovascular, renal, ocular, and neurological complications. Susceptibility to type II diabetes is generally believed to be inherited as a complex polygenic trait. However, a distinct subset of early onset type II diabetes (maturity onset diabetes of the young: MODY) is transmitted as an autosomal dominant monogenic disorder (Tattersall and Fajans, 1975, *Diabetes,* 24: 44–53). The identification of genes implicated in MODY can be regarded as an effective strategy to gain insight into the molecular pathogenesis of the more common and complex late onset forms of type II diabetes mellitus. To date, three distinct MODY genetic loci have been identified (Froguel et al., 1992, *Nature,* 356: 162–164), two of which correspond to transcription factors expressed in pancreatic β-cells [HNF1α (MODY3) and HNF4α (MODY1)]. MODY2 is caused by mutations in the glucokinase gene.

Insulin promoter factor-1 (IPF-1) is a transcription factor known to mediate glucose-responsive stimulation of insulin gene expression and is necessary for pancreas development. This homeodomain protein, also known as IDX-1, STF-1 and PDX-1, is critical for development of the pancreas in mice and is a key factor for the regulation of the insulin gene in the β-cells of the endocrine pancreas (Miller et al., 1994, *EMBO J.,* 13: 1145–1156; Leonard et al., 1993, *Mol. Endocr.,* 7: 1275–1283; Ohlsson et al., 1993, *EMBO J.* 12: 4251–4259; Jonnson et al., 1994, *Nature,* 371: 606–609; Peshavaria et al., 1994, *Mol. Endocr.* 8: 806–816; Peers et al., 1994, *Mol. Endocr..* 8: 1798–1806). Targeted disruption of the Ipf1 gene encoding IPF-1 in transgenic mice results in a failure of the pancreas to develop (pancreatic agenesis), although heterozygosity for this mutation and the wild-type allele has no apparent deleterious consequence (Jonnson, 1994, supra; Offield et al., 1996, *Development,* 122: 983–995). An object of the present invention comprises a screening assay by which to assess a patient's risk of developing MODY4, to distinguish between MODY4 and other forms of MODY and to assist in determining the genetic basis for other pancreatic disorders that might result from IPF-1 deficiency.

SUMMARY OF THE INVENTION

The invention is based on the discovery that a mutation of the IPF1 gene (herein referred to as an "IPF1 mutation"), which encodes the insulin promoter factor-1 (IPF-1) transcription factor, is indicative of pancreatic disease, in particular of form early onset type II diabetes and of pancreatic agenesis.

By "IPF1 mutation", we mean any defect in the IPF1 gene or regulatory regions (promoter, intron, splice sites) which leads to a loss of biological activity of the native IPF-1 protein or to a novel or altered IPF-1 protein function. Such activity includes, but is not limited to, the transcriptional activation of a gene whose regulatory sequences comprise an IPF-1 binding motif, as defined herein.

As used herein, "pancreatic disease" is defined as encompassing the absence, underdevelopment or maldevelopment of the pancreas, or loss or impairment of pancreatic function in terms of either the production, storage, stability or secretion of factors such as proteins, lipids, carbohydrates or other messenger molecules essential for the homeostatic regulation of pancreatic functions. Such factors might include hormones, enzymes, fatty acids, proteins or derivatized proteins such as lipoproteins, glycoproteins or phosphoproteins. Specifically, "pancreatic disease" is used to denote pancreatic agenesis or malformation, diabetes or any other manifestation of disease due to malfunctioning of the pancreas.

"Mature onset diabetes of the young" or "MODY" is a term which refers to a particular subset of cases of type II diabetes, namely those in which the patient becomes diabetic at an early age, typically before age 25, but in which fasting hyperglycemia, if present, can be regulated without insulin for at least two years following onset of clinical symptoms and in which genetic transmission of the disease is by an autosomal dominant mechanism.

"MODY4" refers to MODY that has an IPF1 mutation as its underlying genetic cause.

"IPF-1 binding motif" is defined as any gene regulatory sequence to which IPF-1 binds specifically in order to regulate transcription of the associated gene. Such sequences include, but are not limited to: FAR-FLAT (also called INS1-FLAT), the Far-linked AT-rich element of the rat insulin 1 gene (5'-GATCCTTCTTAATCTAATTACCCTAGGTCTAA-3') [SEQ ID NO: 17]; SMS-TAAT1, a FLAT-like element 438 to 461 nucleotides upstream of the rat somatostatin gene (5'-GATCCCTGATTGCATATTAATTCTCAGATA-3') [SEQ ID NO: 18]; SMS-TAAT2, a FLAT-like element 290 to 303 nucleotides upstream of the rat somatostatin gene (5'-GATCCGATCTCAGTAATTAATCATGCACCA-3') [SEQ ID NO: 19]; SMS-UE-B, the B domain of the rat somatostatin upstream enhancer (5'-GATCCGCGAGGCTAATGGTGCGTAAAAGCACTG GTGA-3') [SEQ ID NO: 20]; and SMS-PS, a transcriptional silencer element 219–233 nucleotides upstream of the rat somatostatin gene (5'-GATCCAGGCAAGATTATTTGGTCA-3') [SEQ ID NO: 21].

The invention comprises a procedure for screening for pancreatic disease in a patient, comprising performing a detection step for a mutation in the gene encoding insulin promoter factor 1, wherein detection of a mutation is indicative of pancreatic disease.

In a preferred embodiment, the further step is carried out of obtaining a positive result in which said patient is homozygous for a mutation in IPF1, homozygosity being indicative of pancreatic agenesis.

It is preferable that a further step is carried out of obtaining a positive result in which said patient is heterozygous for a mutation in IPF1, heterozygosity being indicative of the presence of diabetes mellitus, more preferable that said diabetes mellitus is of the form early onset type II and most preferable that said diabetes mellitus of said form early onset type II is mature onset diabetes of the young (MODY).

Preferably, the mutation in IPF1 is a deletion of a single base pair, more preferably, the mutation results in a translational frame shift, and most preferably, the mutation is IPF1ΔC (also denoted Pro63fsΔC or Pro63fsdelC).

A further object of the present invention encompasses a method for screening a patient for a mutation in the gene encoding insulin promoter factor 1 (IPF-1), comprising the steps of providing a nucleic acid sample from said patient and detecting a mutation in said gene in said sample, wherein detection of a mutation is indicative of pancreatic disease.

It is contemplated that the family of said patient comprises individuals affected with pancreatic disease, that said patient is asymptomatic with regard to pancreatic disease.

In another preferred embodiment, said patient is afflicted with symptoms of pancreatic disease. Preferably, said symptoms of pancreatic disease are those of diabetes mellitus, more preferably of said diabetes mellitus of the form early onset type II, and most preferably of mature onset diabetes of the young (MODY).

It is contemplated that said nucleic acid sample used according to the inventive method is genomic DNA, and preferred that the method comprise a step, after the step of providing said sample, wherein a PCR product of the IPF1 gene of said genomic DNA is generated for use in said detection step.

It is also contemplated that said nucleic acid sample used according to the inventive method is mRNA, and preferred that the method comprise the steps, after the step of providing said sample, wherein a reverse transcript of said mRNA is generated and a PCR product of the IPF1 gene is made from said reverse transcript for use in the said detection step.

It is preferred that said detection step using said PCR product comprises DNA sequencing or single-strand conformation polymorphism analysis.

A further object of the present invention is a method for screening a plurality of patients for a mutation in the gene encoding insulin promoter factor 1 (IPF-1) comprising the steps of providing a plurality of nucleic acid samples from a corresponding plurality of patients and detecting a mutation in said plurality of samples, wherein detection of said mutation in said sample is indicative of pancreatic disease in a said corresponding patient.

It is preferred that said nucleic acid sample is genomic DNA.

It is contemplated that said plurality of patients comprises a group of unrelated individuals. It is preferred that said plurality of patients comprises a group of related individuals.

It is additionally preferred that said mutation in the gene encoding IPF-1 is detected in a patient selected from said plurality of patients who is asymptomatic with regard to pancreatic disease.

It is preferable that said pancreatic disease is diabetes mellitus, more preferable that said diabetes mellitus is of the form early onset type II, highly preferable that said diabetes of the form early onset type II is MODY, and most preferable that said MODY is of the type MODY4.

It is also contemplated that said mutation is detected in said gene encoding IPF-1 in a patient selected from said plurality of patients who shows observable clinical manifestations of pancreatic disease.

It is preferable that said pancreatic disease is diabetes mellitus, more preferable that said diabetes mellitus is of the form early onset type II and highly preferable that said diabetes of the form early onset type II is MODY.

Most preferably, said patient selected form said plurality of patients who shows observable clinical manifestations of MODY has MODY4.

Another object of the present invention is a method of testing a patient who is afflicted with MODY to determine whether or not said patient has MODY4, comprising performing a detection step for a mutation in the gene encoding insulin promoter factor 1, wherein detection of a mutation is indicative of MODY4.

The invention also encompasses a method of screening for pancreatic disease in a patient whose parents both carry an inactivating mutation in the gene encoding IPF-1, comprising performing a detection step for a mutation in the gene encoding IPF-1, wherein detection of a said mutation is indicative of pancreatic disease.

It is preferred that the method further comprises the step of obtaining a result in which said patient is heterozygous for said mutation, heterozygosity being indicative of MODY4.

It is also preferred that the method further comprises the step of obtaining a result in which said patient is homozygous for said mutation, homozygosity being indicative of pancreatic agenesis.

Preferably, said testing according to said method is prenatal.

It is also contemplated that said testing according to said method is postnatal.

The invention also encompasses a method for testing in a patient both alleles of the gene encoding IPF-1 for a mutation, comprising the steps of providing a nucleic acid sample from said patient performing a detection step for a mutation in said gene encoding IPF-1 and detecting a mutation in one or both allelic copies of said gene in said sample wherein homozygosity of a mutation is indicative of pancreatic agenesis and heterozygosity of a mutation is indicative of MODY4.

Preferably, the detection steps of said method comprise the steps of hybridizing to said nucleic acid sample equimolar amounts of labeled oligonucleotide probes unique to wild-type and mutant IPF1 sequences under conditions that permit specific hybridization of each to its target sequence, and comparing quantitatively the extent of hybridization of the two probes to molecules present in said nucleic acid sample, wherein non-hybridization of the wild-type probe indicates homozygosity for the mutant allele and non-hybridization of the mutant probe indicates homozygosity for the wild-type, while a 1:1 ratio of hybridization of wild-type and mutant probes indicates heterozygosity for the two alleles at said locus.

In a preferred embodiment, said testing is performed prenatally.

It is also preferred that said testing is performed postnatally.

In another preferred embodiment, the detection steps of said method comprise the steps of amplifying by PCR a region of said gene encoding IPF-1 to make amplified products that encompass said mutation, cloning the products of said PCR and performing DNA sequence analysis on multiple, independent clones resulting from said cloning to detect the presence or absence of a mutation in each such clone, wherein the failure to detect more than one sequence from among the clones resulting from a given sample is indicative of homozygosity at that locus.

It is also preferred that the detection steps of said method comprise the steps of amplifying by PCR a region of said gene encoding IPF-1 to make amplified products that encompass said mutation and performing single-strand comformation polymorphism (SSCP) analysis on said amplified products, wherein observation of one conformer is indicative of homozygosity and two conformers is indicative of heterozygosity at said locus.

Another object of the present invention is an isolated nucleic acid comprising the nucleotide sequence of SEQ ID NO: 1 with a cytosine deletion at any one of bases 202 through 207.

BRIEF DESCRIPTIONS OF THE DRAWINGS

FIGS. 1(A) through 1(C) depict the organization of the human IPF1 gene. FIG. 1(B) presents a partial human IPF1 sequence [SEQ ID NO: 1, nucleotides 196–210].

FIGS. 2(A) through 2(E) depict the predicted functional consequence of the single cytosine deletion in codon 63. FIG. 2(A) presents partial coding nucleic acid sequence of the human IPF1 gene [SEQ ID NO: 1, nucleotides 200–391], partial wild-type IPF1 amino acid sequence [SEQ ID NO: 2, amino acids 61–124] and partial IPF1ΔC amino acid sequence [SEQ ID NO: 3].

FIG. 3 shows the results of cotransfection into RIN 5AH insulinoma cells of a rat insulin-1 promoter CAT reporter construct and a vector control (basal), wild-type (WT) IPF-1 or mutant (MUT) IPF-1 expression plasmid.

FIG. 4 presents the transmission of IPF1ΔC in two families with MODY.

FIG. 5 depicts the genotype analysis of proband and her parents with microsatellite markers flanking the IPF1 gene.

FIGS. 6(A) through 6(D) depict analysis of the C-terminal translation product of the mutant IPF1 sequence.

FIG. 7 presents the nucleotide sequence of exon 1 of the IPF1 gene [SEQ ID NO: 1], and translated regions of open reading frames 1 [SEQ ID NO: 2], 2 [SEQ ID NO: 3] and 3 [SEQ ID NO: 16].

DETAILED DESCRIPTION OF THE INVENTION

Figure 1A:
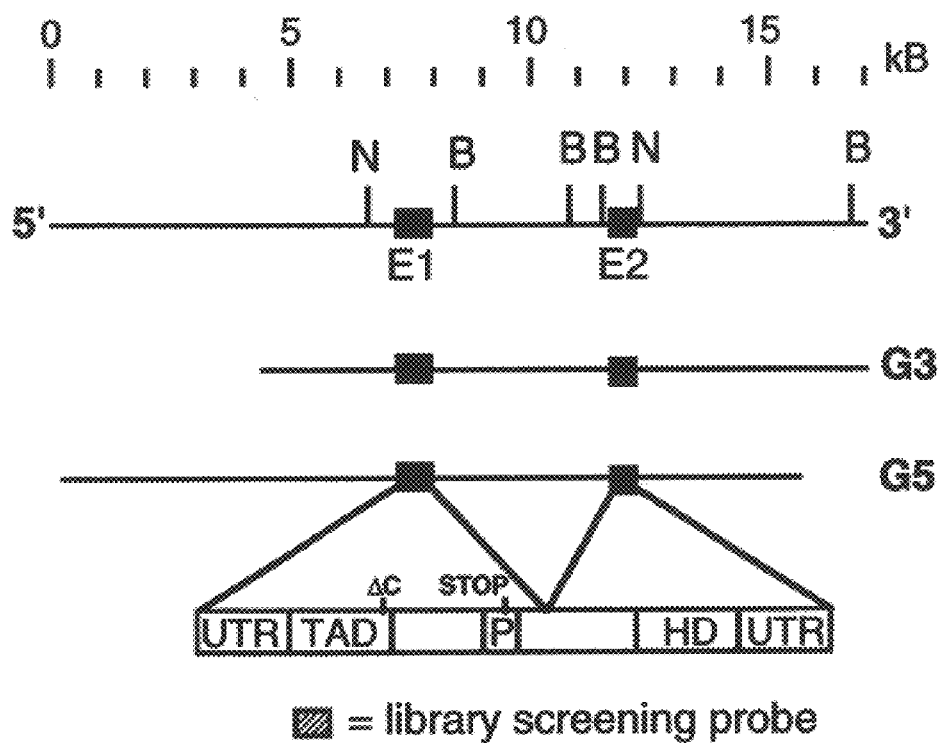

We have developed a molecular genetic screening assay for pancreatic disease in a patient or for risk of pancreatic disease based upon detection of inactivating mutations in the gene encoding the insulin promoter factor-1, a transcription factor that mediates pancreatic development and function. This assay comprises detection of a mutation in a nucleic acid sample derived from a peripheral blood sample drawn from a patient, as described below.

Pancreatic agenesis in humans is a rare disorder; only 8 cases have been reported in the literature (Wright et al., 1993, *Am. J. Dis. Child.,* 147: 607–609; Howard et al., 1980, *J. Pediat.* 97: 786–789; Widnes et al., 1982, *J. Pediat.* 100: 926; Lemons et al., 1979, *Pediatrics,* 64: 255–257; Mehes and Vamosk, 1976, *Acta Paediat. Acad. Sci. Hung.,* 17: 175–176; Dourov and Buyl-Strouvens, 1969, *Arch. Fr. Pediat.,* 26: 641–650; Sherwood et al., 1995, *Pediat. Res.,* 8: 360). Recently, a female Caucasian infant was described in which the diagnosis of pancreatic agenesis was made shortly after birth and appropriate therapy was instituted (Wright et al., 1993, supra). The infant was underweight for gestational age and presented with neonatal diabetes mellitus at birth and, at age 18 days, with pancreatic exocrine insufficiency. By ultrasound examination, the pancreas was absent. After replacement of insulin and pancreatic enzymes was begun, she developed normally and continues to do well at 5 years of age. As described in Example 1, we performed a genetic screening assay on this patient for a mutation in the gene encoding IPF-1 and found that the congenital pancreatic agenesis in this subject was attributable to homozygosity for an inactivating mutation in exon 1 of the protein coding sequence of the IPF1 gene (IPF1ΔC) (Stoffers et al., 1997, *Nature Genetics,* 15: 106–110). Example 2 describes allele-specific hybridization analysis of IPF1, while Example 3 presents single-strand conformation polymorphism analysis, both for the purpose of either detecting a mutation or determining its dosage in the patient. In Example 4, use of the present invention in the detection of a mutation in IPF1 in a plurality of individuals, whether in the course of population studies or in pedigree analysis, is demonstrated. Example 5 illustrates use of the invention to assign linkage of a case of MODY to a particular genetic locus. In Example 6, an extended haplotype analysis using IPF1 and closely-linked chromosomal markers is presented. In Example 7, a C-terminal translation product of the mutant IPF1 gene is examined.

METHODS OF THE INVENTION

Methods enabling use of the present invention are described in detail in Examples 1 and 2. They include the polymerase chain reaction, DNA sequence analysis, allele-specific hybridization, single-strand conformation polymorphism analysis, mammalian cell culture and transfection, in vitro protein expression, Western blotting, Northern analysis, reverse transcription, Southern analysis and statistical methods, as described. While these techniques are commonly known in the art, the invention encompasses their use in the detection of a mutation in the IPF-1 gene for clinical diagnostic applications.

EXAMPLE 1

Genomic cloning of human IPF1.

To examine the patient's IPF1 gene for the presence of mutations, it was necessary to determine the nucleotide sequence of the normal human gene. 500,000 recombinant phage from a human genomic library (HUVEC, λ DASH II, Stratagene, Inc., La Jolla, Calif.) were screened using a $^{32}$P-labeled PCR-generated probe corresponding to the 5' end of the open reading frame in the mouse Ipf1 cDNA (FIG. 1; hatched box) using standard methods (Sambrook et al., 1989, *Molecular Cloning: A Laboratory Manual,* Cold Spring Harbor Laboratory Press, New York). This probe was chosen because of the high degree of sequence similarity between rat and mouse IDX-1/IPF-1-encoding cDNAs in this region and to avoid the homeodomain that is highly conserved among all members of the homeodomain protein family. Southern blot analysis of human genomic DNA hybridized to this probe revealed a single band, indicating the likelihood that a single human gene contains sequences homologous to this probe. Four rounds of screening resulted in two plaque-purified clones, G3 and G5, from which phage DNA was prepared. Phage inserts were mapped by Southern analysis of partial restriction enzyme digests with $^{32}$P-labeled oligonucleotide probes complementary to phage sequences adjacent to the cloning site of λ DASH II. FIG. 1A presents a restriction map of overlapping genomic phage inserts, G3 and G5, showing the restriction sites of NotI (N) and BamHI (B). The library screening probe is indicated by a hatched rectangle. The putative positions of the exons are denoted E1 and E2. The structure of the mRNA is shown (open box), where UTR represents the untranslated region, TAD the transactivation domain, P the pentapeptide PBX interaction motif and HD the homeodomain.

Figure 9:
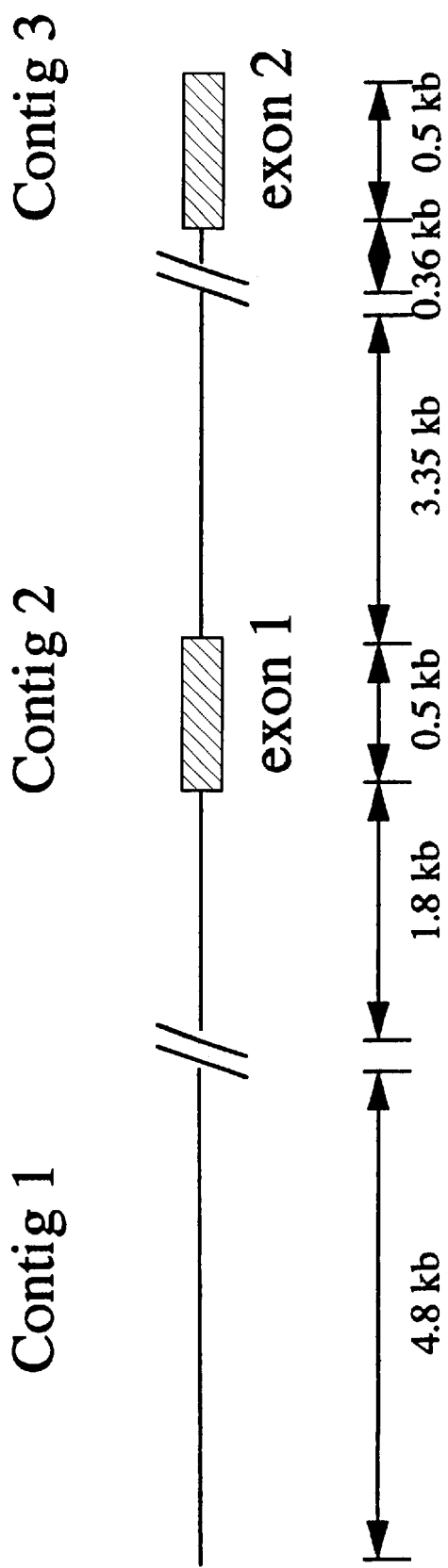
FIG. 9 is a schematic representation of the IPF1 gene, indicating the locations of three regions of genomic sequence, Contig 1 [SEQ ID NO: 22], Contig 2 [SEQ ID NO: 23] and Contig 3 [SEQ ID NO: 24].

The two human genomic phage clones representing overlapping segments of the human IPF1 gene isolated in this screen were partially sequenced after mapping. The contig consists of 15 kb and encompasses the entire coding region, which consists of 2 exons based on a comparison with the human cDNA sequence (Stoffel et al., 1995, *Genomics*, 28: 125–126; Inoue et al., 1996, *Gene. Diabetes*, 45: 789–794), as shown in FIG. 1A. A schematic representation of the IPF1 gene that indicates the locations of three blocks of genomic sequence, denoted contig 1 [SEQ ID NO: 22], contig 2 [SEQ ID NO: 23] and contig 3 [SEQ ID NO: 24], is presented in FIG. 9. The coding sequences of the human and mouse genes exhibit 100% amino acid identity in the homeodomain and high (86%) amino acid homology in the flanking domains.

Analysis of patient DNA

Genomic DNA was isolated from peripheral blood samples of the patient, parents and normal control subjects by standard methods (Sambrook et al., 1989, supra). The nucleotide sequence of both exons was determined after PCR amplification of the patient's genomic DNA and subcloning of the amplified fragments. PCR amplification of exon 1 was performed in 2 sequential rounds using nested primers.

Round 1 primers were:

PCR4:   5' GGAATTCGGCTGTGGTTCCCTCT 3' [SEQ ID NO: 4]

and

S16:    5' CAGAGAGAAGGCTCCTG    3'.[SEQ ID NO: 5]

Round 2 primers were:

S17b:   5' AGCGAGCAGGGGTGGCG 3'  [SEQ ID NO: 6]

and

S18:    5' GGGACGCTTGGAGGTAA 3'.  [SEQ ID NO: 7]

Each round consisted of 26 cycles with denaturation at 97.5° C. for 15 sec, annealing at 60° C. for 90 sec, and extension at 72° C. for 2 min. Where indicated, the resultant fragment (610 bp) was subcloned (TA cloning vector PCRII; Invitrogen) and sequenced (Sequenase 2.0; United States Biochemicals, Cleveland, Ohio). Exon 2 screening was performed in 3 overlapping PCR fragments. The sequences of the primer pairs employed were as follows:

(A) PCR2: 5' CGGGATCCGCCGAGCTTCTTGTC 3' and [SEQ ID NO: 8]

PCR3: 5' GGATTCTGGGGCTTGGTGGCTC 3' [SEQ ID NO: 9]

($T_{ann}$ = 60° C.)

(B) S1: 5' CGCCTACGCTGCGGAGC 3' and [SEQ ID NO: 10]

S14: 5' AGAAGCTCCTCGCCGGAG 3' [SEQ ID NO: 11]

($T_{ann}$ = 37° C.)

(C) S12: 5' AGGAGGAGGACAAGAAGC 3' and [SEQ ID NO: 12]

PCR7: 5' CGGATCCTAGGGCCTCTGCTCC 3' [SEQ ID NO: 13]

($T_{ann}$ = 37° C.)

Figure 1B:
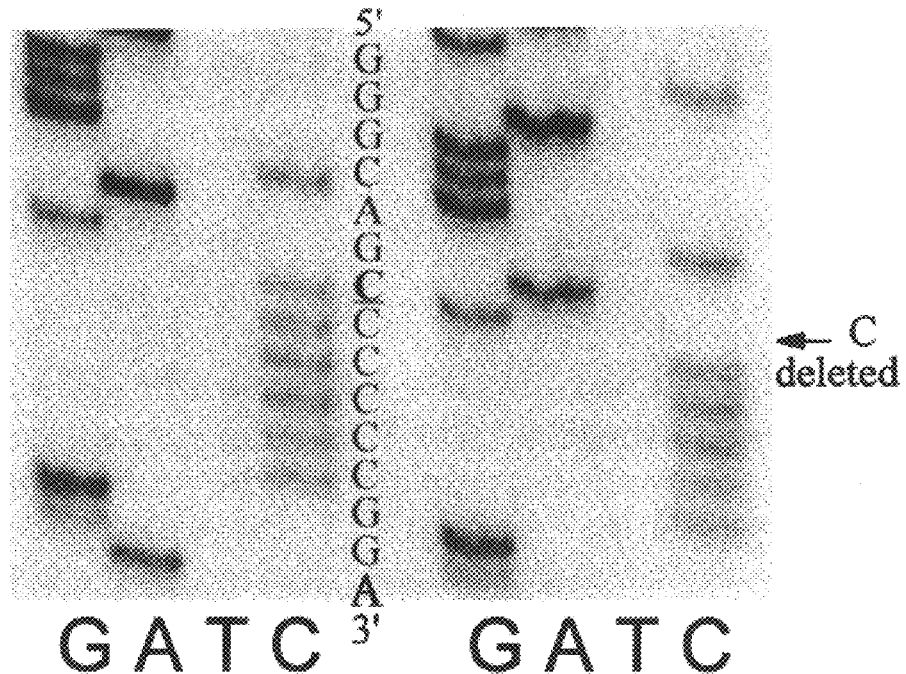
Figure 1C:
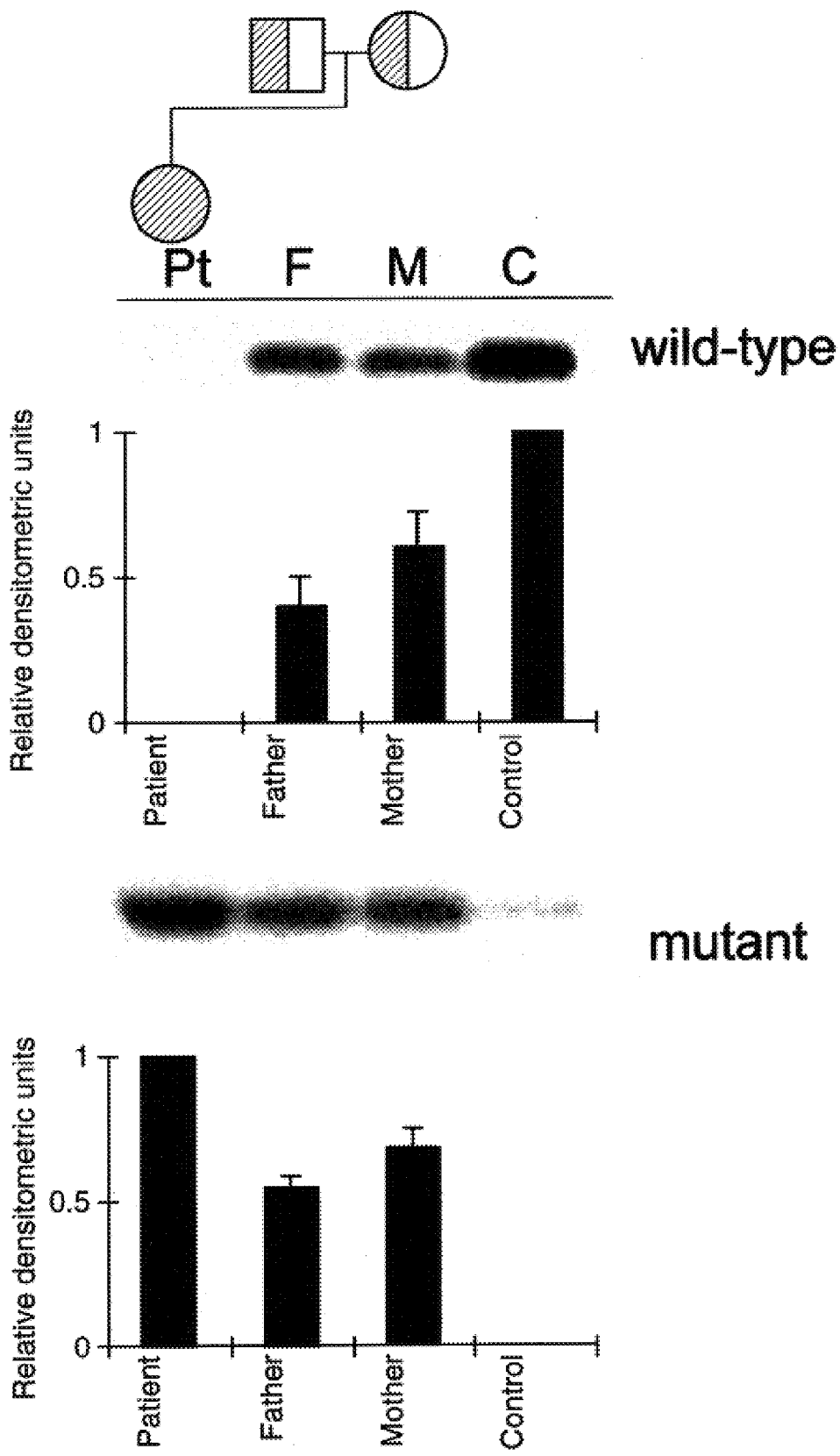

A deletion of a single cytosine was found in codon 63 of exon 1 resulting in a frame shift of translation that terminates 59 codons downstream; the DNA sequences of an exon 1 PCR subclone from a control subject (left) and from the affected patient (right) in this region are shown in FIG. 1B, where the deleted cytosine in the patient's DNA is indicated with an arrow. In order to confirm that the IPF1ΔC mutation leads to a loss of IPF-1 function and, consequently, the patient's pancreatic deficiency, it was necessary to analyze the mutant IPF-1 protein.

Analysis of the IPF1 mutant protein.

The deletion of a cytosine in codon 63 of human IPF1 results in a frameshift beginning at the C-terminal border of the transactivation domain of IPF-1. A truncated protein comprising 121 amino acids, with an approximate molecular weight of 13.2 kDa, is predicted. In FIG. 2A, the nucleotide sequence beginning at codon 61 through the premature stop codon is shown [SEQ ID NO: 1], and the deleted cytosine in codon 63 is underlined. The amino acid sequence of the wild type reading frame [SEQ ID NO: 2] is shown above the nucleotide sequence, and the frame shifted reading frame is shown below [SEQ ID NO: 3]. The premature stop codon overlapping codon 122 is indicated by an asterisk (*). FIG. 2B diagrams the mutant protein. The positions of the transactivation (TA) and DNA binding domains (homeodomain, HD) are indicated. The novel sequence resulting from the frame shift is indicated in the hatched box. The conceptualized protein terminates amino-proximal to the essential DNA binding domain, so is missing the homeodomain as well as the FPWMK motif required for the interaction with another homeoprotein, PBX (Peers et al., 1995, *Mol. Cell. Biol.* 15: 7091–7097), but retains the transactivation domain required for synergistic interaction with transcription factor E47 in the transcriptional regulation of the insulin gene (Peers et al., 1994, supra). It was predicted that the truncated protein would not be transported to the nucleus, because the nuclear localization signal resides in the homeodomain (Lu et al., 1996, *Endocrinology*, 137: 2959–2967), and so would not interfere with normal IPF-1 function.

To determine directly whether the conceptual translational reading frame imposed by the cytosine deletion in codon 63 results in termination after 59 additional codons, expression plasmids that contained the wild-type sequence and the mutation were prepared and transfected into Cos-1 cells, and their expressed protein products analyzed. Since a full-length human IPF1 cDNA was not available, a fusion Idx1/IPF1 expression construct was created in which the unique conserved AflIII site was used to fuse exon 1 from human IPF1 in frame to the remainder of exon 1 and exon 2 of rat Idx1 cDNA (Miller et al., 1994, supra). The wild-type human IPF1 portion was the 0.5 kb EcoRI-AflIII fragment from a fully sequenced TA subclone of a nonaffected individual, while the mutation-containing first exon fragment was taken from a sequenced TA subclone from the proband. Thus, the 5' end of the open reading frame including the mutation, the ensuing 59 codons and the premature stop codon are all derived from human IPF1. The rat derived portion was the 0.9 kb AflIII-BamHI fragment of rat Idx1 pBJ5 (Lu et al., 1996, supra). These fragments were ligated into the EcoRI and BamHI double-digested eukaryotic expression vector pcmv5 (Chen et al., 1991, Cell 66: 327–334). The amino-terminal IDX-1/IPF-1 antiserum ($\alpha$251) was a rabbit polyclonal antiserum raised against the the first 12 amino acids of rat IDX-1 (100% conserved between rat and human). Two carboxy-terminal antisera were utilized, Hm66 ($\alpha$66) directed against GST IDX-1 (164–283) which recognizes predominantly homeodomain sequences and $\alpha$253, directed against the carboxy-terminal 12 amino acids of IDX-1/IPF-1. Transfections into Cos-1 cells were performed using diethylaminoethyl-dextran and a brief dimethylsulfoxide shock (Ausubel et al., 1995, *Current Protocols in Molecular Biology*, John Wiley and Sons, New York).

Figure 2C:
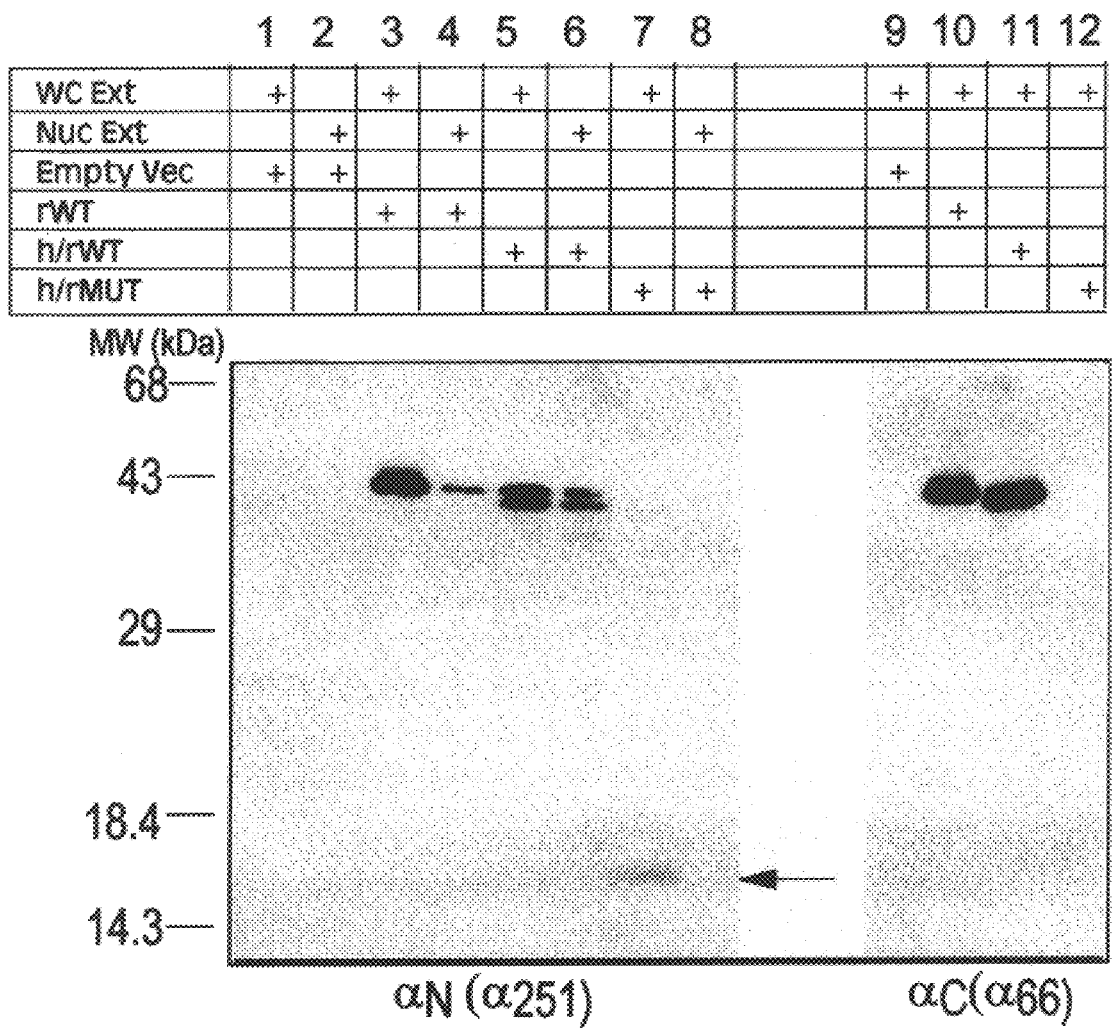

Western blot analysis was performed as follows: Whole cell lysates were prepared from transfected Cos-1 cells by lysing freshly isolated cells in SDS sample buffer. Lysates were sonicated, then cleared by centrifugation (10,000×G, 4° C.). Nuclear extracts were prepared by the method of Dignam et al. (1983, *Nucleic Acids Res.*, 11: 1475–1489). Extracts and lysates were fractionated on SDS-polyacrylamide gels and electroblotted onto nitrocellulose membranes (MSI; Westborough, Mass.). The membranes were incubated with 1:20,000 dilutions of primary antisera and, subsequently, with an alkaline phosphatase-conjugated goat anti-rabbit secondary antibody (BioRad Laboratories; Richmond, Calif.). Immunoreactive proteins were visualized using the ECL chemiluminescent detection system (Amersham, Inc.; Arlington Heights, Ill.), as shown in FIG. 2C. Results from whole cell extracts are presented (WC Ext; lanes 1, 3, 5 and 7) as are those of nuclear extracts (Nuc Ext; lanes 2, 4, 6 and 8) prepared from Cos-1 cells transfected with pcmv5 (Empty Vec; lanes 1 and 2), rat IDX-1pBJ5 (rWT; lanes 3 and 4), wild-type human IPF-1/rat IDX-1 (h/rWT; lanes 5 and 6) and $\Delta$C mutant human IPF-1/rat IDX-1 (h/rMUT; lanes 7 and 8). All are probed with $\alpha$251 against the amino terminus of IDX-1/IPF-1. Whole cell extracts from Cos-1 cells transfected with pcmv5 (lane 9), rat IDX-1pBJ5 (lane 10), wild type human IPF-1/rat IDX-1 (lane 11) and $\Delta$C mutant human IPF-1/rat IDX-1 (lane 12) are probed with $\alpha$66 against carboxy-terminal IDX-1/IPF-1 sequences.

Figure 2D:
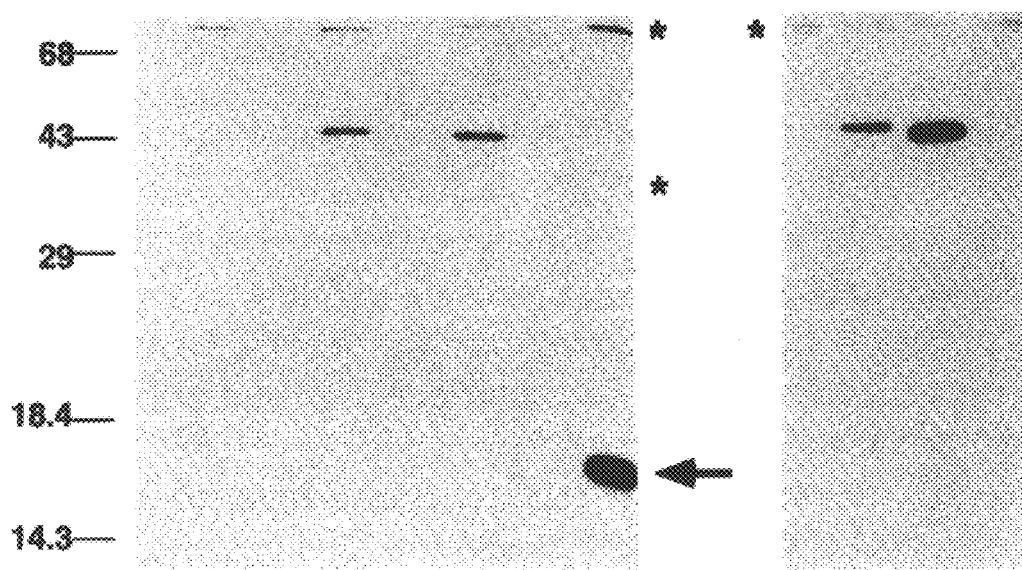

For immunoprecipitations, cells were labeled with $^{35}$S methionine/cysteine (Trans $^{35}$S-label, ICN) for 1 hour prior to harvesting. Analysis of whole cell lysates was carried out as previously described (Ron and Habener, 1992, *Genes Dev.* 6: 439–453) using the amino- and carboxy-terminal antisera described above. FIG. 2D depicts immunoprecipitation of $^{35}$S-labeled proteins from transfected Cos-1 cells with pre-immune antiserum $\alpha$PI (lanes 1, 3, 5 and 7) and $\alpha$251 (lanes 2, 4, 6 and 8). Immunoprecipitates are from cells transfected with pcmv5 (Empty Vec; lanes 1 and 2), rat IDX-1pBJ5 (lane 3 and 4), wild type human IPF-1/rat IDX-1 (lane 5 and 6) and $\Delta$C mutant human IPF-1/rat IDX-1 (lane 7 and 8). $^{35}$S-labeled proteins from whole cell extracts of transfected Cos-1 cells (pcmv5, lane 9; rat IDX-1pBJ5, lane 10; wild-type human IPF-1/rat IDX-1, lane 11; $\Delta$C mutant human IPF-1/rat IDX-1, lane 12) using antiserum $\alpha$253 were also examined. The truncated protein is indicated by an arrow. Asterisks (*) denote non-specific cross-reacting proteins endogenous to Cos-1 cells.

Figure 2E:
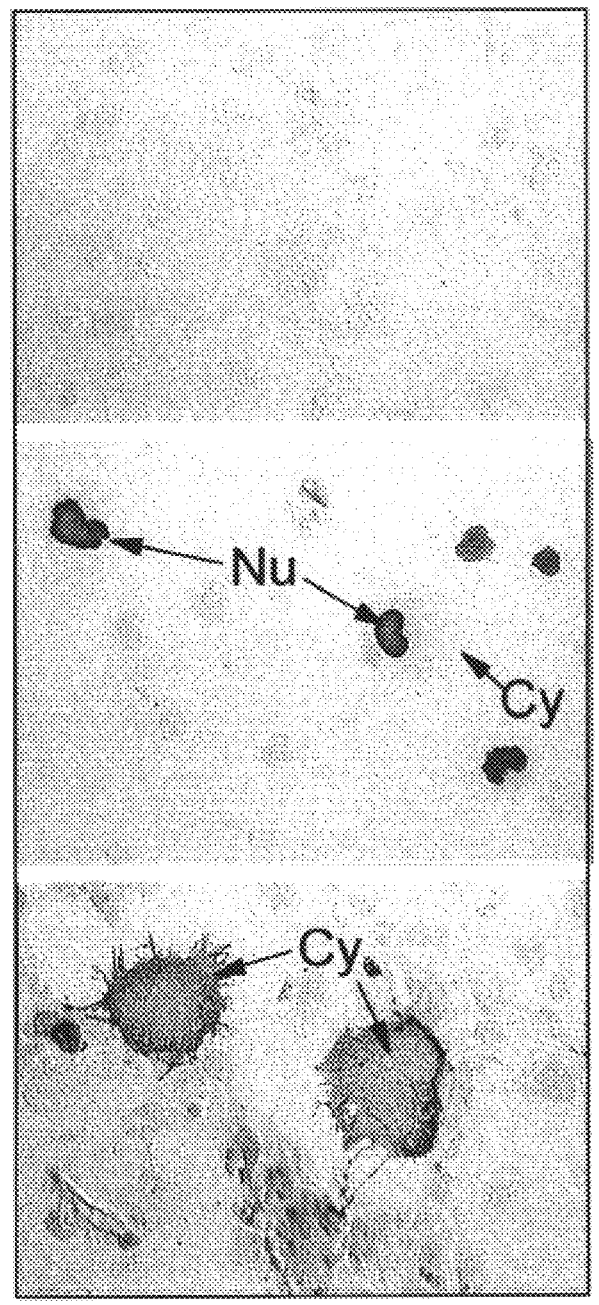

Transfected Cos-1 cells were examined by immunocytochemistry using the amino-terminal antiserum ($\alpha$251) as follows: Cos-1 cells grown on chamber slides (Falcon; Oxnard, Calif.) were fixed with 4% paraformaldehyde in phosphate-buffered saline, permeablized in acetone at −20° C. and incubated overnight in $\alpha$251. In order to visualize the antibody/IPF-1 complex, slides were incubated with a biotinylated secondary antibody, followed by an avidin-conjugated horseradish peroxidase complex (Vectastain ABC System, Vector Laboratories; Burlingame, Calif.). Immunocytochemistry of transfected Cos-1 cells stained with pre-immune serum (top) or $\alpha$251 (N-terminal) (wild-type IDX-1I/IPF-1, center and mutant IDX-1/IPF-1, bottom) is shown in FIG. 2E. Examples of nuclei (Nu) and cytoplasm (Cy) are indicated (arrows).

Antiserum $\alpha$251 detected proteins of 42–43 kDa by Western blot analysis (FIG. 2C, lanes 3 and 5) and by immunoprecipitation (FIG. 2D, lanes 4 and 6) in Cos-1 cells transfected with wild-type IDX-1/IPF-1 plasmids. These proteins are also detected by a carboxy terminal specific antiserum (FIG. 2C, lanes 10 and 11) and are present in nuclear extracts (FIG. 2C, lanes 4 and 6). In contrast, Cos-1 cells transfected with an IDX-1/IPF-1 expression plasmid harboring the cytosine deletion in codon 63 expressed only a 16 kDa protein (FIG. 2C, lane7 and FIG. 2D, lane 8). This protein was not detected in nuclear extracts (FIG. 2C, lane 8) and could not be visualized with a C-terminal specific antiserum (FIG. 2C, lane 12 and FIG. 2D, lane 12). The predicted cytoplasmic localization of the truncated protein was confirmed by immunocytochemistry of transfected Cos-1 cells using the amino-terminal antiserum (FIG. 2E). Expression of wild-type IDX-1/IPF-1 was entirely nuclear (center panel), while mutant IDX-1/IPF-1 had a striking distribution throughout the cytoplasm (bottom panel). By electrophoretic mobility shift assays, transfected cell nuclear extracts showed the expected binding to known IDX-1/IPF-1 binding sites for wild type IDX-1I/IPF-1 proteins but failed to show specific binding in nuclear extracts from mutant Idx1/IPF1-transfected cells (data not shown). These data indicate that a truncated protein lacking the homeodomain (and nuclear localization signal) is produced as a result of the mutation.

Figure 3:
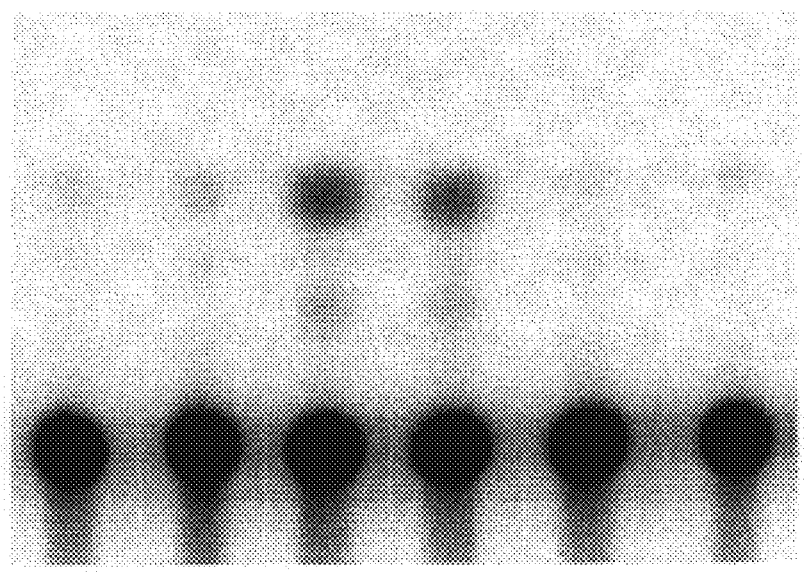

The SMS-TAAT1 promoter element [SEQ ID NO: 18] of the somatostatin gene is an IPF-1 target sequence. Other such sequences are the SMS-TAAT2 [SEQ ID NO: 19], SMS-UE-B [SEQ ID NO: 20] (Vallejo et al., 1992, *J. Biol. Chem.* 267: 12868–12876) and SMS-PS [SEQ ID NO: 21] regulatory elements of the rat somatostatin gene and the FAR-FLAT (INS1-FLAT) [SEQ ID NO: 17] regulatory element of the rat insulin 1 gene (German et al., 1992, *Mol. Cell. Biol.*, 12: 1777). To confirm the supposition that the truncated mutant protein is unable to transactivate, RIN5AH insulinoma cells were cotransfected by DEAE-dextran in suspension with the SMS-TAAT1-65SMS CAT reporter, in which the TAAT1 element drives expression of the bacterial chloramphenicol acetyl-transferase gene, and either vector alone (basal), wild-type (WT) IPF-1 or mutant (MUT) Idx1/IPF1 expression plasmid (FIG. 3). Only the wild-type fusion protein directed transcription of the CATgene, as indicated by CAT enzymatic activity measured as percent of conversion (acetylation) of $^{14}$C-labeled chloramphenicol.

Together, these findings establish that the IPF1ΔC mutation results in the production of a truncated protein that has undergone the loss of a biological function and is, therefore, an inactivating mutation at that genetic locus.

EXAMPLE 2

Allele-specific hybridization analysis of IPF1.

The cytosine deletion in codon 63 of the IPF1 gene of the apancreatic patient described in the first example was observed in 100% of PCR subclones of exon 1 (Table 1) suggesting homozygosity. Evidence for this deletion was obtained using 4 different sequencing primers which revealed the point deletion on both DNA strands of the PCR subclones, confirming that it was not a cloning artifact. No mutations were detected in exon 2. The patient has no siblings; however, analysis of the parents' genomic DNA indicates that each parent is heterozygous for the same cytosine deletion in codon 63. Approximately half of the exon 1 PCR subclones from each parent possess the point deletion (Table 1).

TABLE 1

| Subject | # PCR subclones analyzed | # Clones with DC in codon 63 (%) |
| --- | --- | --- |
| Patient | 16 | 16 (100) |
| Father | 13 | 8 (61) |
| Mother | 12 | 6 (50) |
| Normal Control | 14 | 0 (0) |

(Number and % of exon 1 PCR subclones analyzed possessing the point deletion for the patient, both parents and a normal control).

While the results such as are presented in Table 1 are valid, an assay which requires sequencing of multiple PCR clones derived from each patient in order to determine whether they are homozygous or heterozygous for a mutation in IPF1 is of limited clinical utility, as the procedure is time-consuming and expensive; this is particularly true when pedigree analysis is undertaken, as numerous subjects must be screened. Since no restriction enzyme site was gained or lost as a result of this point deletion, conditions were optimized for allele-specific hybridization to confirm the homozygous versus heterozygous presence of the mutation in the patient and her parents. The conditions were as follows:

Equal amounts of DNA were loaded in each lane of an agarose gel, verified by quantitation of ethidium bromide fluorescence prior to Southern transfer. Wild-type (5' ATGTCCGGGGGGCTGCC 3') [SEQ ID NO: 14] and mutation-specific (5' CAGGGCAGCCCCCGGAC 3') [SEQ ID NO: 15] oligonucleotides were end-labeled with T4 polynucleotide kinase and $\lambda^{32}$P-ATP. Hybridizations were performed with 2–3×10$^6$ cpm/ml of labeled oligonucleotide in 6×SSC, 5×Denhardt's solution, 1% SDS, 50 mM sodium phosphate, pH 6.8 and 100 μg/ml denatured salmon sperm DNA at 37° C. for 6–15 hours. Washes were: 4×10 min in 5×SSC, 0.1% SDS at room temperature, followed by 1×10 min in 5×SSC, 0.1% SDS at 37° C., 2×30 min in 3M tetramethylammonium chloride, 50 mM Tris, pH 8.0, 0.2% SDS at 52° C. followed by a brief rinse in 2×SSC, 0.1% SDS at room temperature (Wood et al., 1985, *Proc. Natl. Acad. Sci. USA*, 82: 1585–1588).

Both parents exhibited an intermediate intensity of hybridization to the wild-type sequence and mutation-specific oligonucleotides, supporting heterozygote status. The affected patient exhibited no hybridization with the wild-type oligonucleotide, while the normal control subject had no hybridization with the mutation specific oligonucleotide. These results are summarized in FIG. 1C, where Southern blots used for allele-specific hybridization, performed to confirm the mutation status in the patient (PA), both parents (F=father, M=mother) and a normal control (N) are shown, along with graphs below each blot that represent densitometry of autoradiograms and/or quantitation of phosphorimager scans. The pedigree is depicted above the results. In the case of the wild-type oligonucleotide probe (n=2), the patient's density of hybridization was set to 0.0 and the normal to 1.0 (based on sequencing of PCR subclones; see Table 1) after an initial background correction. Conversely, for the mutation-specific oligonucleotide (n=4), the patient's density of hybridization was set to 1.0 and that of the normal control to 0.0. Similar results were obtained when the higher fidelity Pfu DNA polymerase was employed in the PCR reactions. Collectively, these data indicate that the parents are heterozygous, while the proband is homozygous, for the cytosine deletion in codon 63.

EXAMPLE 3

Single-strand conformation polymorphism analysis.

One approach to detecting multiple allelic isoforms of a gene resulting from single base mutations in an organism or plurality of organisms is single strand conformation polymorphism (SSCP) (Glavac et al., 1993, *Hum. Mut.*, 2:404; Sheffield et al., 1993, *Genomics*, 16:325). SSCP is a simple and effective technique for the detection of single base mutations. This technique, with which one can simultaneously screen a patient for the presence and allelic copy number of a mutation in IPF1, is based on the principle that single-stranded DNA molecules take on unique sequence-based secondary structures (conformers) under nondenaturing conditions. Molecules differing by as little as a single base substitution may form different conformers which assume different electrophoretic mobility profiles in a nondenaturing polyacrylamide gel. The genomic region to be screened for sequence polymorphisms is first amplified by PCR in each sample to be compared. Single-base substitutions as well as short insertions or deletions lying within the probe region (between the PCR primers) can be detected efficiently. Although the nature of a given mutation is not revealed by this technique, the presence of a mutation within the amplified region is made apparent, allowing for further molecular analysis. This technique has proven useful for detection of multiple mutations and polymorphisms. SSCP sensitivity varies dramatically with the size of the DNA fragment being analyzed. The optimal size fragment for sensitive detection by SSCP is approximately 150–300 bp.

Typically, electrophoresis of single-stranded DNA is performed under denaturing conditions that maintain the single strandedness of the molecules. Common denaturants are urea, formamide and sodium hydroxide. The SSCP gel is unconventional in that single-stranded DNA is loaded on gel that lacks a denaturant. Small molecules would ordinarily pass through the pores of the gel matrix more easily than large molecules and migrate faster. In a denaturing gel, intramolecular interactions occur, and single-stranded DNA is able partially to self-anneal; therefore, its mobility is governed by both size and tertiary structure (conformation). The technique is performed as follows:

One or more test nucleic acid samples are prepared for PCR amplification. Oligonucleotide primers are synthesized by standard methods. Nested PCR amplification of the first exon of IPF1 is performed as described above, using primers PCR4 [SEQ ID NO: 4] and S16 [SEQ ID NO: 5] in the first round and S17b [SEQ ID NO: 6], except that in the second round, amplification and radiolabeling are performed concurrently. A typical deoxynucleotide mix would include 0.2 mM of non-radioactive dGTP, dATP, dTTP, 0.02 mM of non-radioactive dCTP and 0.05 ml of [$\alpha$-$^{33}$P] dCTP (1,000–3,000 Ci/mmol; 10 mCi/ml).

SSCP analysis is performed as follows. Ten $\mu$l of formamide dye (95% formamide, 20 mM EDTA, 0.05% bromophenol blue, 0.05% xylene cyanol) are added to 10 $\mu$l of radioactive PCR products. The reactions are denatured at 100° C. for 5 min, then quenched on ice. Two $\mu$l are loaded onto a gel containing 8% acrylamide:bisacrylamide (37.5:1), 0.5×TBE (45 mM Tris-borate, 1 mM EDTA) and 5% glycerol and electrophoresed in 0.5×TBE at 25W for 8 hours at 4° C. Dried gels are exposed to X-OMAT ARfilm (Kodak) and the autoradiographs are scored for the presence of bands that do not co-migrate with those generated by a wild-type control nucleic acid sample, which is run side-by-side with test samples; a sample with an aberrant electrophoretic profile contains a mutation in the region of interest. SSCP may be optimized, as desired (Glavac et al., 1993, supra).

It is also advantageous to examine nucleic acid samples for mutations in IPF1 using fluorescent SSCP (fSSCP) assays (Makino et al., 1992, *PCR Methods Appl.* 2:10; Ellison et al., 1993, *Biotechniques*, 15:684). In the second round of nested PCR amplification, fluorescently-labeled deoxynucleotides can be incorporated and the reaction products visualized and analyzed using an ABI fluorescent DNA sequencing machine. Four distinct fluorochromes now available can be used for different primer pairs, and by differentially labeling the test and control PCR products, the two samples can be loaded into the same lane of a gel for direct comparison, eliminating lane-to-lane variations in gel resistance and, consequently, the rate of sample migration. A major advantage of fSSCP over SSCP is that the latter requires handling of radioactive materials whereas fSSCP does not. Data collection is automated, and data analysis programs can be used to identify aberrantly-migrating samples, whereas SSCP evaluation involves visual examination, and correction for lane-to-lane variations in electrophoretic conditions is not possible. fSSCP analysis is performed as follows.

Amplifications are performed as above, except that a standard deoxynucleotide mix (0.2 mM of dGTP, dATP, dTTP, dCTP) is employed and each second-round reaction contains a primer labeled with one of the fluorochromes HEX, FAM, TET or JOE. Two $\mu$l of fluorescent PCR products are added to 3 ul formamide dye (95% formamide, 20 mM EDTA, 0.05% bromophenol blue, 0.05% xylene cyanol), denatured at 100° C. for 5 min., then chilled. As an internal standard, 0.5–1 ml of Genescan™ 1500 size markers is added, then 2 $\mu$l of the mix are loaded onto a gel containing 8% or 10% acrylamide:bisacrylamide (37.5:1), 0.5×TBE (45 mM Tris-borate, 1 mM EDTA) and 5% glycerol. Electrophoresis is performed in 0.5×TBE at 4° to 10° C. at 2500–3500 volts for 4 to 10 hours on an ABI 377 DNA sequencing machine. Data is automatically recorded and analyzed with Genescan™ and Genotype analysis software (ABI). As with radioactive SSCP, peaks of fluroescence that vary in electrophoretic mobility relative to those of control samples indicate the presence of a mutation.

In the case either of SSCP or fSSCP, the fragment which shows the aberrant migration is amplified again from the mutated nucleic acid sample using unlabeled primers and sequenced according to standard molecular methods.

EXAMPLE 4

The present invention can be used for screening a plurality of individuals for defects in the IPF1 gene. In this manner, the invention is useful both in population genetics research and in linkage analysis of IPF1 mutations and pancreatic disease in a candidate pedigree. It was decided to determine the frequency of occurrence of the IPF1$\Delta$C mutation in a population of unaffected subjects. We used the mutation-specific oligonucleotide under the hybridization conditions employed in Example 2 to screen genomic DNA from 92 normal control subjects, representing 184 independent chromosomes, for the presence of the cytosine deletion. This mutation was not detected in any of the control subjects, decreasing the likelihood that the point deletion is simply a DNA sequence polymorphism. Given the rarity of the IPF1$\Delta$C allele and the high incidence of early-onset diabetes in both branches of the proband's family, it was decided to determine whether or not the risk of diabetes is linked to the $\Delta$C mutation in this pedigree.

Genomic DNA was prepared from peripheral blood samples of 27 members of this pedigree, and Exon 1 of the IPF1 gene was amplified using nested primers PCR4 [SEQ ID NO: 4] and S16 [SEQ ID NO: 5] in the first round and S17b [SEQ ID NO: 6] and S18 [SEQ ID NO: 7] in the second, according to the protocol described in Example 1, and allele-specific hybridization was performed on the PCR product using primers of the wild-type [SEQ ID NO: 14] and mutant [SEQ ID NO: 15] IPF1 sequences, as described above in Example 2. As in previously reported MODY pedigrees, the disease follows an autosomal dominant mode of transmission with age-dependent penetrance in six generations. The average age of onset is 35 years (range 17–67) and 6 of 8 affected heterozygotes are treated with diet and/or oral hypoglycemic agents.

Linkage results were analyzed with MLINK and ILINK programs from the LINKAGE package version 5.1, under a model of autosomal dominant inheritance. A disease gene frequency of 0.01 and equal male to female recombination was assumed. Marker allele frequencies were estimated from the genotypes observed within the MODY4 pedigree. For the IPF1$\Delta$C allele, the frequency was set at 0.001. Two-point LOD scores were insensitive to modifications of disease gene frequencies to 0.01–0.0001, and to setting marker allele frequencies at 1/n, where n is the total number of alleles for a given marker. To account for the age-dependent penetrance of MODY and the existence of phenocopies caused by sporadic late-onset diabetes, LOD scores were calculated using 4 liability classes stratified by age of onset for affected subjects or age of last clinical assessment for unaffected subjects): I, <15; II, 15–30; III, 30–60; IV, >60 years. Penetrance was set at 0, 0.5, 1, and 1 for susceptible genotypes, on the basis of the mean age of diagnosis in affected individuals of this pedigree (35 years). LOD score calculations remained >3 with variations of penetrance in class II between values 0.2–0.8. Penetrance for nonsusceptible homozygotes was set at 0.001, 0.001, 0.005, 0.05. These values are based on prevalence rates of diabetes in U.S. Caucasians (National Diabetes Data Group in Diabetes in America; National Institutes of Health, Bethesda, 1995). Similar assumptions have been used in previous linkage studies for MODY1, 2 and 3 (Froguel et al., 1992, supra; Hattersley et al., 1992, *Lancet*, 339: 1307–1310; Zhang et al., 1995, *Diabetologia*, 38: 1055–1060; Bowden et al., 1992, *Am.J.Hum.Genet.*, 50: 607–618; Bell et al., 1991, Proc. Natl. Acad. Sci. USA 88: 1484–1488; Menzel et al., 1995, *Diabetes*, 44: 1408–1413).

Figure 4:
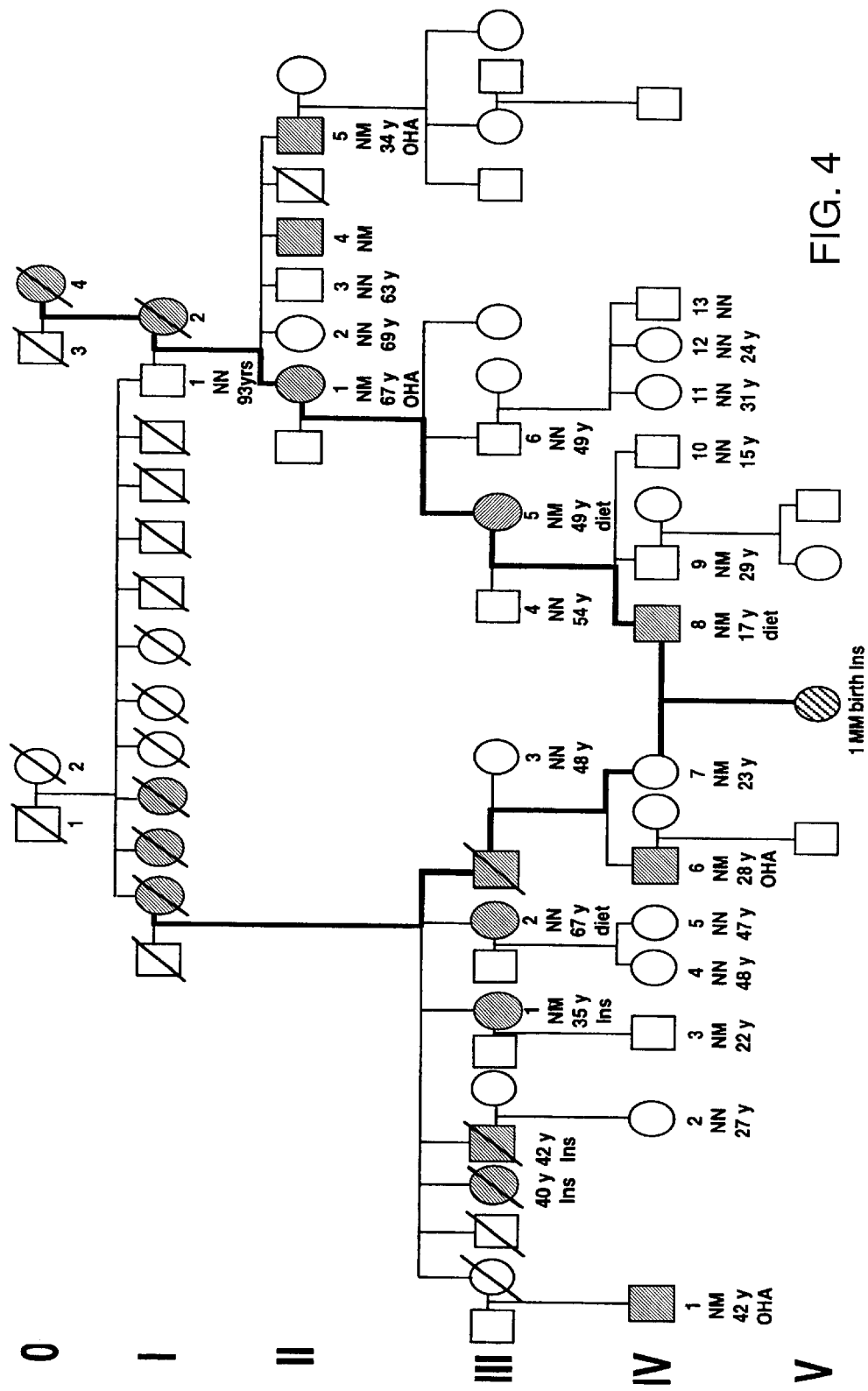

The results are presented in FIG. 4. The subjects are identified by generation number (along left margin) and individual numbers within each generation (upper left of symbols). Diabetic phenotype is indicated by filled symbols. The shaded symbol indicates impaired glucose tolerance. Genotype is indicated below the identification number (N=normal sequence allele, M=allele with IPF1ΔC mutation). The sixth generation offspring is homozygous for IPF1ΔC and has pancreatic agenesis and diabetes as well as exocrine pancreatic efficiency (indicated by a hatched circle). Age at diagnosis of diabetes or age of ascertainment (if unaffected) is indicated below the genotype. Treatment modality is indicated below the age (OHA=oral hypoglycemic agent, Ins=insulin).

The IPF1ΔC mutation segregated with early-onset diabetes in both branches of the pedigree, and two-point LOD scores provided significant evidence for linkage to this locus (Z=3.43, θ=0). Although one consanguinous loop is observed in this pedigree, subject I-1 is not diabetic and carries two normal alleles, suggesting that 1–2 transmitted the mutation and may thus also be genetically related to I-1. Consistent with this circumstance, both I-2 and her mother were diabetic. Subject III-5 had glucose intolerance and carried the IPF1ΔC mutation. Three unaffected individuals heterozygous for IPF1ΔC are under age 30, but are well within the age range at which diabetes develops in this family. Subject III-2 is diabetic but does not carry the mutant allele. Because she has late-onset type II diabetes (age of diagnosis 67 years), she is likely to represent a phenocopy. Sporadic late-onset diabetes has been observed in all forms of MODY where the genetic defect is known (Froguel et al., 1992, supra; Hattersley et al., 1992, supra; Yamagata et al., 1996, *Nature*, 384: 455–458; Yamagata et al., 1996, Nature, 384: 458–460; Velho et al., 1997, *Diabetologia*, 40: 217–224).

EXAMPLE 5

To assess for linkage to MODY1, 2 and 3, amplification of simple sequence repeat polymorphisms of markers closely linked to them was performed using standard PCR conditions. These markers included ADAPR (MODY1), GCK1 and GCK2 (MODY2) and D12S76 (MODY3). One of each pair of primers was end-labeled with $\lambda^{32}$P-ATP and T4 polynucleotide kinase (Promega Corp.; Madison, Wis.) and 0.5 μl of labeled primer was included in each 15 μl PCR reaction. The amplified products were resolved on a 6% denaturing sequencing gel, the gel was dried and exposed to film. The observed alleles were independently scored by two individuals.

When family members were genotyped with these markers, all resulted in negative LOD scores at low recombination values (Table 2). These observations provide evidence that diabetes in this family is not linked to any of the three previously characterized MODY loci. Based on the clinical phenotype, the mode of transmission, and the linkage analysis results, it is apparent that IPF1 represents a new genetic locus of diabetes, MODY4.

EXAMPLE 6

Figure 5:
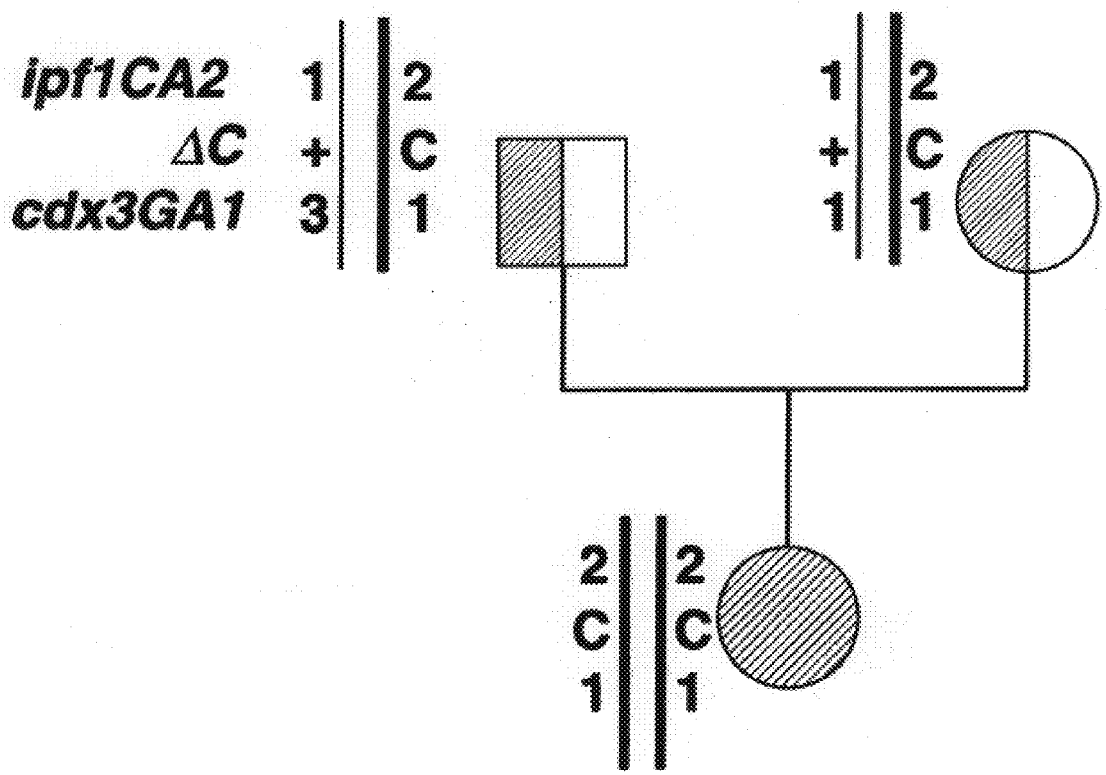
Figure 5:
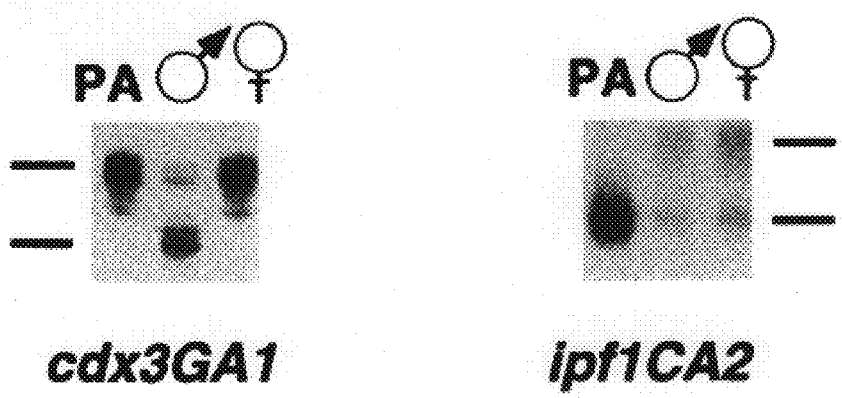

Interestingly, two of the eight reported cases of pancreatic agenesis, referenced above, involved siblings (Sherwood et al., 1995, supra), while another involved documented consanguinity (Mehes and Vamosk, 1976, supra). These two reports and our data indicate that some cases of pancreatic agenesis are transmitted in an autosomal recessive manner. Given the rarity of pancreatic agenesis, an extended haplotype analysis using two closely linked microsatellite markers (Ipf1CA2 and cdx3GA1; Inoue et al., 1996, *Gene. Diabetes*, 45: 789–794) was performed in the proband and her parents, as well as several unrelated controls. Amplimers and PCR conditions for simple sequence repeat polymorphisms, Ipf1CA2 and cdx3GA1, were as described (Inoue et al., 1996, supra). Diagrammatic representation of scored alleles is shown in in the upper portion of FIG. 5, while the lower portion presents an autoradiogram of end-labeled PCR products resolved on a 5% denaturing sequencing gel (PA, proband; +, wild-type IPF1 allele; C, allele possessing the cytosine deletion in codon 63). For Ipf1CA2, 3 distinct alleles were resolved in the proband, parents and four normal controls. For cdx3GA1 , 5 alleles were observed.

This analysis was consistent with homozygosity by descent of the chromosomal segment containing IPF1-ΔC. Thus, as expected for a rare allele ocurring in the homozygous state, both of the proband's IPF1-ΔC alleles are likely to have been derived from a single common ancestor.

EXAMPLE 7

Figure 6A:
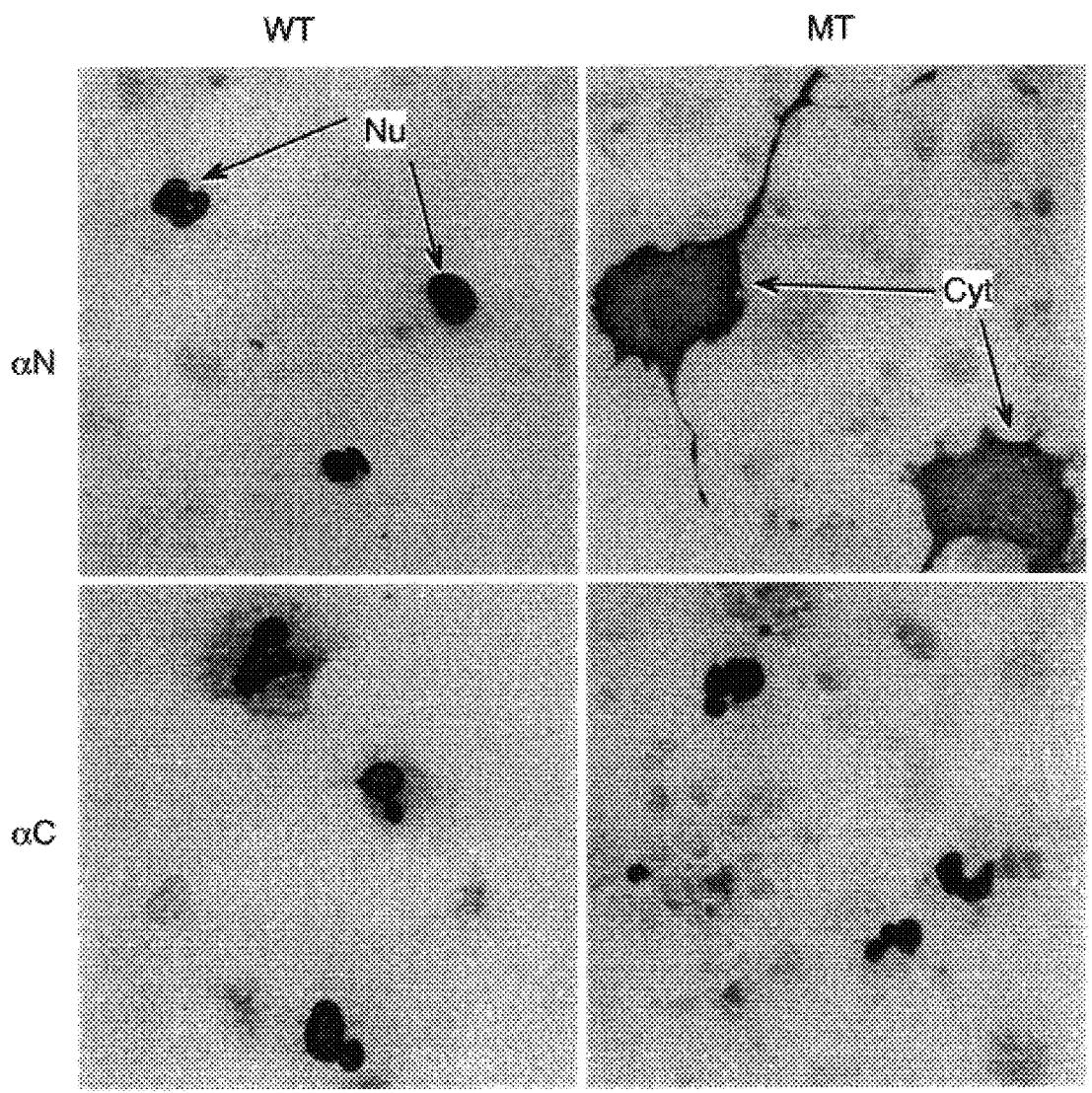
Figure 6B:
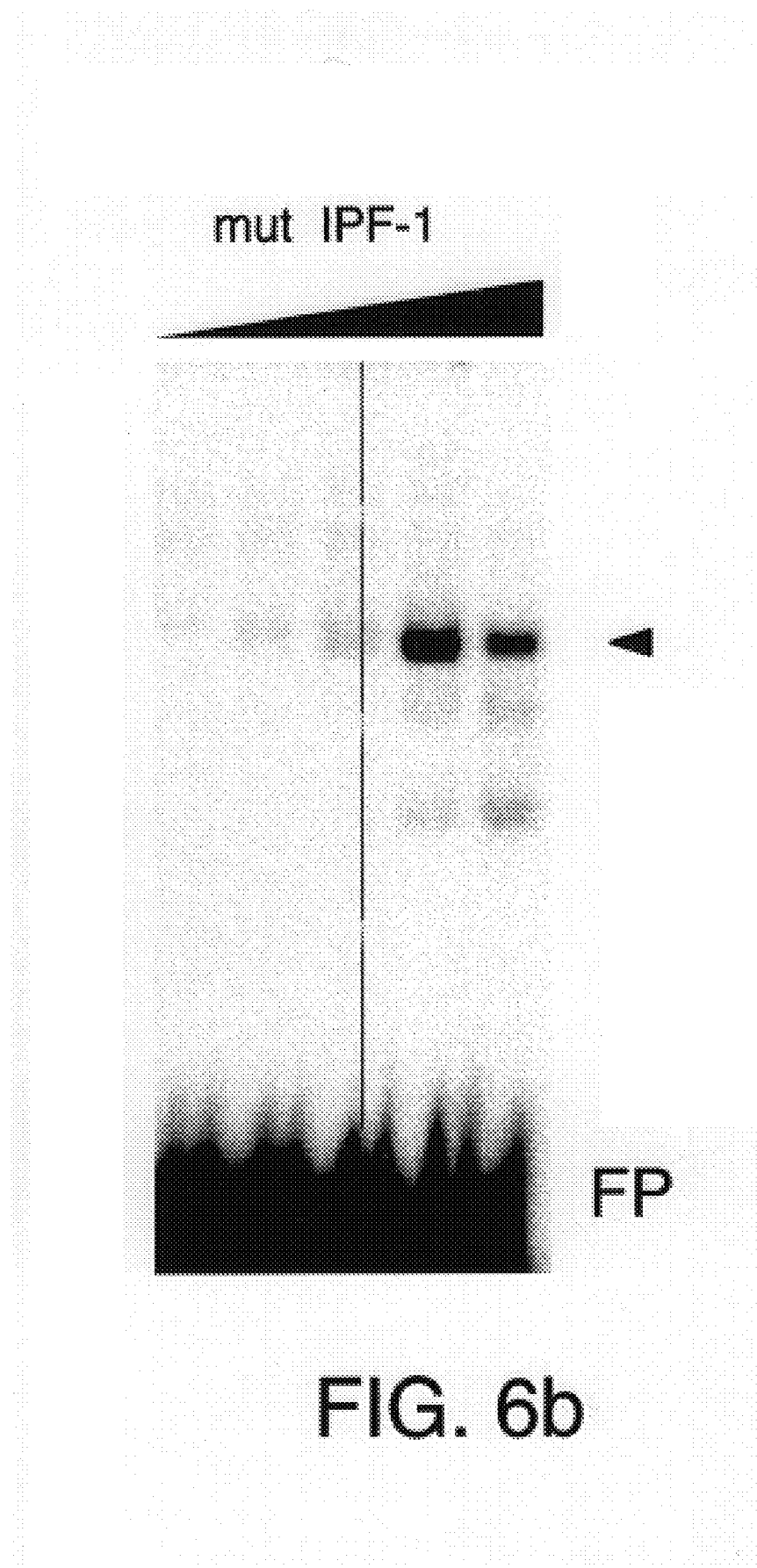

It is clear from the experiments described in Example 1 that the IPF1ΔC mutation results in the premature termination of the translation of IPF-1 and that the truncated product lacks the C-terminal domain of the protein consisting of the homeodomain that contains the DNA-binding and nuclear translocation functions. Subsequent to those experiments, we observed that α-253, the antibody specific for the detection of the C-terminus of IPF-1, detects a protein encoded by the mutated IPF-1 mRNA that translocates to the nucleus. FIG. 6A shows immunocytochemistry of Cos-1 cells transfected with wild-type (left hand panels) or mutant IPF-1 cDNA (right hand panels) stained with N-terminal (αN; upper panels) and C-terminal (αC; lower panels) specific antisera α251 and α253, respectively. Examples of stained nuclei (Nu) and cytoplasm (Cyt) are indicated. It has been shown that IPF-1 is the predominant transcription factor binding to the rat insulin-1 gene glucose-responsive FAR-FLAT enhancer element [SEQ ID NO: 17] (Peers et al., 1994, supra). We performed electrophoretic mobility shift assays on this element according to the method of Miller et al. (1994, supra), using nuclear extracts prepared from baby hamster kidney (BHK) cells that were lipofectin transfected with increasing amounts (1.25–12.5 mg) of expression vectors containing either wild-type IDX1/IPF1 or mutant IDX1/IPF1 cDNA harboring the IPF1ΔC mutation, the construction of which is described above. The mobility shift assay was performed using labeled, double-stranded FAR FLAT element of the rat insulin I promoter as probe. We observed that a translational product of the mutant cDNA binds to this IPF-1-specific element. In FIG. 6B, the specific complex is indicated by an arrow.

Figure 6C:
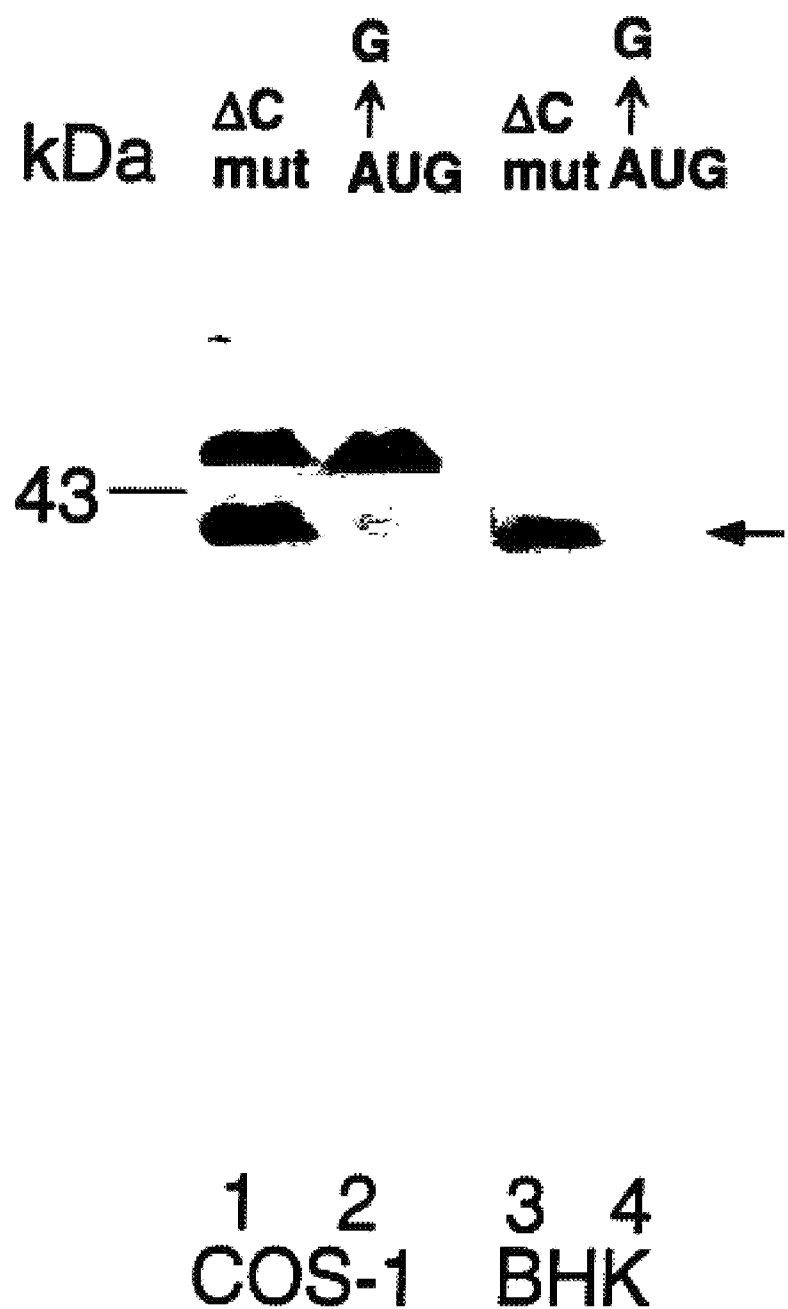
Figure 7:
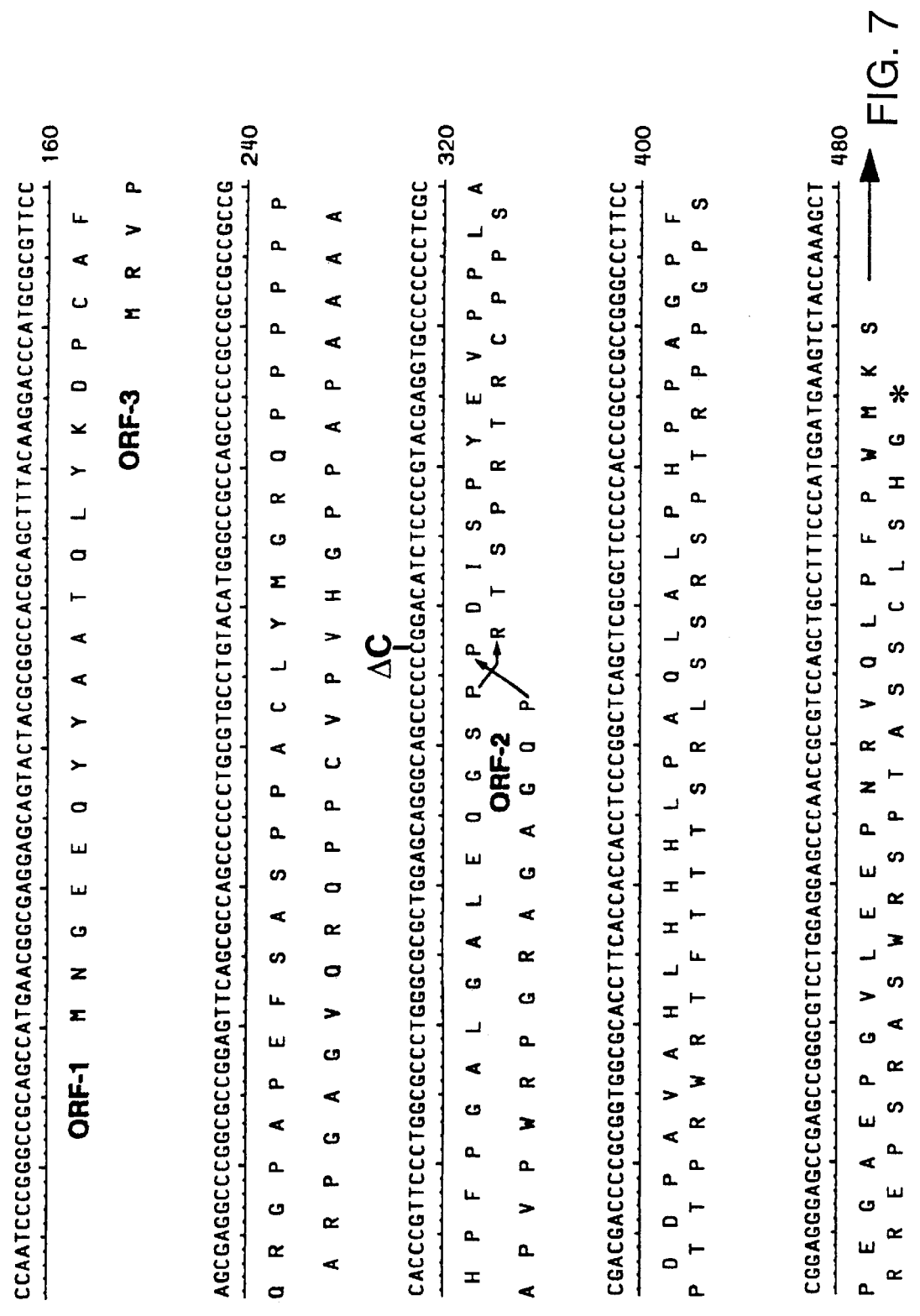
Figure 8:
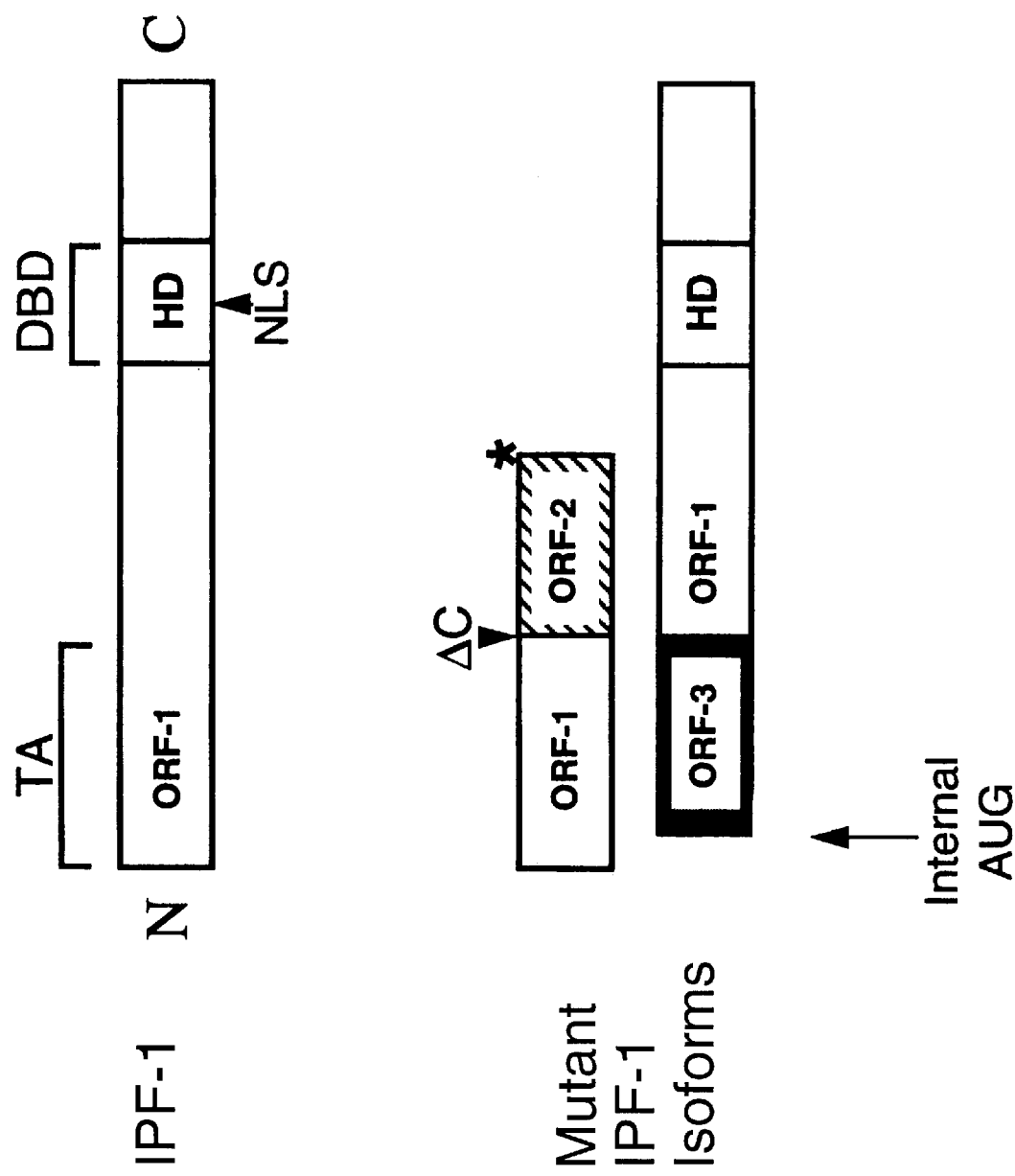
FIG. 8 shows a schematic representation of IPF-1 along with its N- and C-terminal mutant isoforms.

These unanticipated findings prompted us to more closely examine the nucleotide sequence of exon 1 of IPF-1 for the possibility of an internal reinitiation of translation of the mutated IPF-1 mRNA triggered by the premature termination of translation. Such occurrences in the translation of prematurely translated mRNAs are well recognized and are believed to result from the release of ribosomes initiated by 5' upstream AUG start codons thus relieving ribosomal elongation occlusion and allowing for reinitiation of translation at cryptic internal AUG codons in the mRNA (Walker and Habener, 1996, *J. Biol. Chem.* 271: 20145–20150; Kozak, 1995, *Proc. Natl. Acad. Sci. USA* 92: 2662–2666). Upon examination of the nucleotide sequence of the IPF-1 mRNA we found an AUG codon in a favorable context for translational initiation (as defined by Kozak, 1989, *J. Cell Biol.*, 108: 229–241) at nucleotides 51 to 53 and determined that this AUG codon reinitiates translation of the mutant IPF-1 mRNA. Site-directed mutagenesis of the out-of-frame AUG beginning at nucleotide 51 of the IDX1/IPF1 open reading frame was performed such that A was replaced by G at position 51 using the Quik-Change Kit (Stratagene; La Jolla, Calif.). This mutation converted the methionine codon to a valine while leaving the amino acid coding sequence of the N-terminal truncated translation product unchanged; no C-terminal IPF-1 protein is produced in this case. Western blot analysis of nuclear extracts prepared from Cos-1 (lanes 1 and 2) and BHK (lanes 3 and 4) cells transfected with mutant IPF-1 expression plasmid (lanes 1 and 3) and the same plasmid in which the AUG at nucleotides 51–53 was eliminated by site-directed mutagenesis to a GUG (Val) (lanes 2 and 4) is shown in FIG. 6C. The protein band which is lost as a result of the AUG mutation is indicated by an arrow, and the position of the 43 kDa molecular weight marker is indicated. The larger species observed in the Cos-1 extracts is believed to initiate at an upstream site in the polylinker of the expression vector. Although translation is out of the reading frame for IPF-1, the mutation IPF1ΔC in the mutant IPF1 allele shifts and reestablishes the correct reading frame for the protein. FIG. 7 presents the nucleotide sequence of exon 1 [SEQ ID NO: 1] along with the translated regions of the three open reading frames (ORF-1, 2 and 3) [SEQ ID NO: 2, 3 and 16, respectively] in single-letter amino acid code. The position of the IPF1ΔC mutation is indicated by ΔC. A schematic depiction of the two mutant IPF-1 isoforms and the open reading frames which are joined as a result of the cytosine deletion in codon 63 (ΔC) is shown in FIG. 8 (ORF1, open box; ORF2, cross-hatched; ORF3, stippled; TA, transactivation domain; DBD, DNA-binding domain; HD, homeodomain; NLS, nuclear localization signal). The consequence of this translational frameshift is the synthesis of an alternative isoform of IPF-1 that lacks the N-terminal domain critical for the transactivation of gene transcription (Lu et al., 1996, supra; Peers et al., 1994, supra) but possesses the DNA-binding and nuclear translocation signals.

Figure 6D:
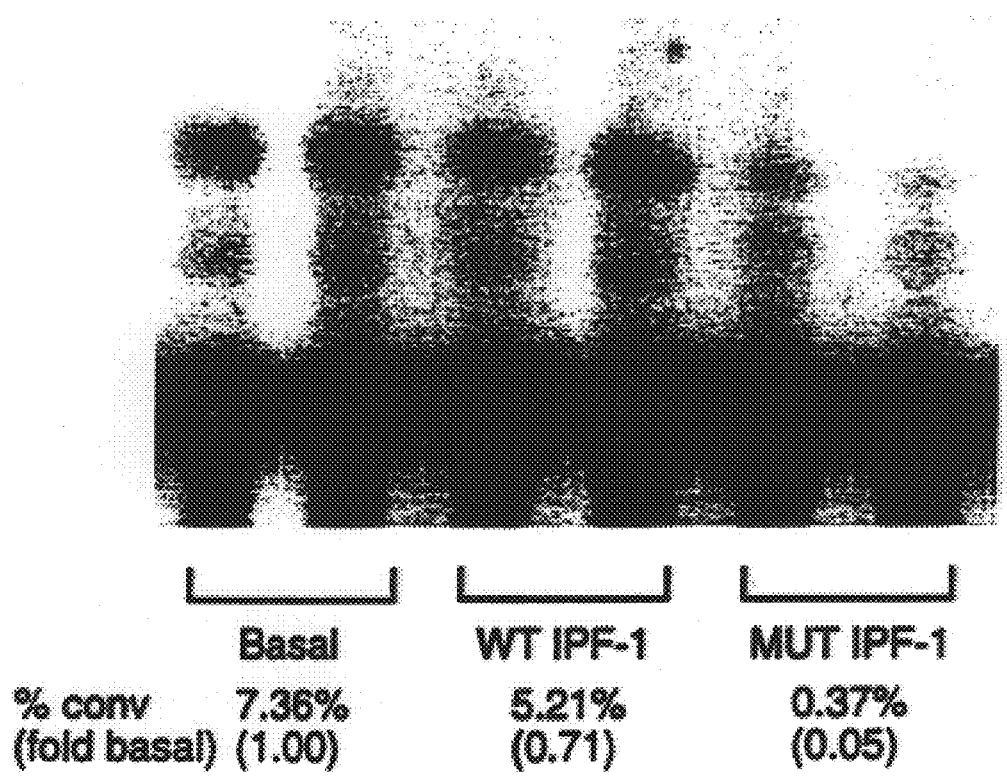

These findings raised the possibility that the N-terminally truncated, internally-translated IPF-1 isoform may serve as a dominant negative inhibitor of the wild type protein expressed from the unaffected IPF1 allele. To test this assumption, RIN5AH insulinoma cells were transfected by DEAE-dextran in suspension with expression plasmid containing either the mutant or wild-type Idx1/IPF1 construct along with a rat insulin-1 promoter CAT reporter plasmid. Indeed, the mutant protein is able to reduce basal transcription of a rat insulin 1 reporter in RIN5AH cells (FIG. 6D).

USE

The present invention is of use in the assessment of an individual's risk of developing mature onset diabetes of the young 4 (MODY4), which results from an inactivating defect in the gene encoding insulin promoter factor-1 (IPF-1). Such a genetic screen is particularly valuable in evaluating the prognosis of an individual in whose family early-onset diabetes type II is known to exist.

The invention can be applied to a plurality of subjects, either unrelated individuals or those belonging to an extended family, to establish the linkage between pancreatic disease and mutations in IPF1 in a given population or pedigree.

An additional use of the invention is in the field of genetic couseling. It is advantageous to know the specific genetic basis for an inherited disease, even when risk analysis is not an issue, i.e. when a patient has already become symptomatic. In the case of a disorder that is linked to defects at multiple genetic loci, assignment of the mutation to a specific locus in a given patient can be used when two affected individuals are deciding whether or not to have children together. While both might suffer from MODY, it is not necessarily true that both would have inactivating mutations in IPF1; if not, their child would not be at risk of pancreatic agenesis.

It is further envisioned that the methods of the invention can be applied to prenatal screening for pancreatic agenesis in those cases in which both of the unborn patient's parents are either known to carry- or are suspected of carrying an inactivating mutation in IPF1.

TABLE 2

Pairwise LOD scores for linkage between diabetes in the family pedigree and markers for the MODY 1, 2, and 3 loci and Pro63fsdelC

| Marker | LOD score at recombination fraction (θ) of | | | | | |
| --- | --- | --- | --- | --- | --- | --- |
| | 0 | 0.001 | 0.01 | 0.1 | 0.2 | 0.4 |
| ADAPR (MODY1) | −7.22 | −4.11 | −2.87 | −0.98 | −0.41 | −0.06 |
| GCK1 (MODY2) | −4.86 | −3.84 | −2.68 | −1.06 | −0.56 | −0.11 |
| GCK2 (MODY2) | −2.74 | −2.66 | −1.97 | −0.44 | −0.10 | 0.03 |
| D12S76 (MODY3) | −6.62 | −6.53 | −5.32 | −1.93 | −0.98 | −0.19 |
| Pro63fsdelC | 3.43 | 3.42 | 3.37 | 2.86 | 2.19 | 0.66 |

Maximum 2-point LOD scores for each marker are shown in bold.

What is claimed is:

1. A method for screening for pancreatic disease in a patient, comprising performing a detection step for a deletion at any one of cytosines 202–207 of SEQ ID NO: 1 in the gene encoding insulin promoter factor 1, wherein detection of a said deletion is indicative of pancreatic disease.

2. A method for screening a patient for pancreatic disease, comprising the steps of:
   a) providing a nucleic acid sample from the patient, and
   b) performing a detection step to detect a deletion at any one of cytosines 202–207 of SEQ ID NO: 1 in the gene encoding insulin promoter factor-1 (IPF-1) in the sample, wherein detection of a said deletion is indicative of pancreatic disease.

3. A method for screening a plurality of patients for pancreatic disease, comprising the steps of:
   a) providing a plurality of nucleic acid samples from a corresponding plurality of patients, and
   b) performing a detection step to detect a deletion at any one of cytosines 202–207 of SEQ ID NO: 1 in the gene encoding insulin promoter factor 1 (IPF-1) in the plurality of samples, wherein detection of a said deletion in a said sample of said plurality of nucleic acid samples is indicative of pancreatic disease in a patient of said corresponding plurality of patients.

4. A method of testing a patient who is afflicted with MODY to determine whether or not said patient has MODY4, comprising performing a detection step for a deletion at any one of cytosines 202–207 of SEQ ID NO: 1 in the gene encoding insulin promoter factor 1, wherein detection of a said deletion is indicative of MODY4.

5. A method of screening for pancreatic disease in a patient whose parents both carry an inactivating mutation consisting of a deletion at any one of cytosines 202–207 of SEQ ID NO: 1 in the gene encoding IPF-1, comprising performing a detection step for the mutation in the gene encoding IPF-1, wherein detection of the mutation is indicative of pancreatic disease.

6. A method for testing a patient for pancreatic agenesis or MODY4, comprising the steps of:
   a) providing a nucleic acid sample from said patient,
   b) performing on both allelic copies of the gene encoding insulin promoter factor-1 (IPF-1) a detection step for a deletion at any one of cytosines 202–207 of SEQ ID NO: 1 in said gene, and
   c) detecting a said deletion in one or both of said allelic copies of said gene in said sample, wherein homozygosity of a said mutation is indicative of pancreatic agenesis and heterozygosity of a said mutation is indicative of MODY4.

7. A method for screening for mature onset diabetes of the young (MODY) in a patient, comprising detecting an insulin promoter factor 1 (IPF-1) gene comprising a mutation, wherein said IPF-1 gene comprising a mutation encodes a truncated IPF-1 protein which lacks transactivation function, and wherein detection of heterozygosity for said mutation is indicative of MODY.

8. The method of claim 7, wherein said mutation is a deletion of a base pair.

9. The method of claim 7, wherein said mutation results in a translational frameshift.

10. The method of claim 7, wherein said mutation is IPF1ΔC.

11. A method for screening a patient for MODY, comprising the steps:
    a) providing a nucleic acid sample from said patient, and
    b) detecting an IPF-1 gene comprising a mutation in said sample of step a), wherein said gene comprising a mutation encodes a truncated IPF-1 protein which lacks transactivation function, and wherein detection of heterozygosity for said mutation is indicative of MODY.

12. The method of claim 11, wherein said patient is asymptomatic with regard to MODY.

13. The method of claim 11, wherein said patient is afflicted with symptoms of MODY.

14. The method of claim 11, wherein said nucleic acid sample is genomic DNA.

15. The method of claim 11, comprising a further step after step a) wherein a PCR product of the IPF-1 gene of said genomic DNA is generated for use in the detection of step b).

16. The method of claim 11, wherein said nucleic acid sample is mRNA.

17. The method of claim 16, further comprising the steps after said step a) wherein
    i) a reverse transcript of said mRNA is generated, and
    ii) a PCR product of the IPF-1 gene is made from said reverse transcript for use in the detection of step b).

18. The method of claim 14, 15, 16, or 17, wherein the detection of said mutation in the IPF-1 gene is performed by nucleic acid sequence analysis.

19. The method of claim 15 or 17, wherein the detection of said mutation in the IPF-1 gene is performed by single-strand conformation polymorphism analysis (SSCP).

20. A method for screening a plurality of patients for MODY, comprising the steps:
    a) providing a plurality of nucleic acid samples from a corresponding plurality of patients, and
    b) detecting an IPF-1 gene comprising a mutation in said plurality of samples of step a), wherein said gene comprising a mutation encodes a truncated IPF-1 protein which lacks transactivation function, and wherein detection of heterozygosity for said mutation in a sample of said plurality of samples in indicative MODY in a patient of said plurality of patients.

21. The method of claim 20, wherein said nucleic acid is genomic DNA.

22. The method of claim 21, wherein said plurality of patients comprises a group of unrelated individuals.

23. The method of claim 21, wherein said plurality of patients comprises a group of related individuals.

24. The method of claim 22 or 23, wherein said mutation is detected in said IPF-1 gene in a patient selected from said plurality of patients who is asymptomatic with regard to MODY.

25. The method of claim 24, wherein said MODY is of the type MODY4.

26. The method of claim 23, in which a patient selected from said plurality of patients shows observable clinical manisfestations of MODY.

27. The method of claim 26, in which said patient selected from said plurality of patients who shows observable clinical manifestations of MODY has MODY4.

28. A method of testing a patient who is afflicted with MODY to determine whether or not said patient has MODY4, comprising detecting an IPF-1 gene comprising a mutation, wherein said gene comprising a mutation encodes a truncated IPF-1 protein which lacks transactivation function, and wherein detection of said mutation is indicative of MODY4.

29. A method of screening for MODY in a patient whose parents both carry an inactivating mutation in the gene encoding IPF-1, comprising detecting an IPF-1 gene comprising a mutation, wherein said gene comprising a mutation encodes a truncated IPF-1 protein which lacks transactivation function, and wherein detection of heterozygosity for said mutation is indicative of MODY.

30. The method of claim 29, wherein said MODY is of the type MODY4.

31. The method of claim 29 or 30, wherein said screening is prenatal.

32. The method of claim 29 or 30, wherein said screening is postnatal.

33. A method for testing a patient for MODY4, comprising the steps:
   a) providing a nucleic acid sample from said patient, and
   b) detecting an IPF-1 gene comprising a mutation in said sample of step a), wherein said gene comprising a mutation encodes a truncated IPF-1 protein which lacks transactivation function, and wherein detection of heterozygosity for said mutation is indicative of MODY4.

34. The method of claim 33, wherein said testing is performed prenatally.

35. The method of claim 33, wherein said testing is performed postnatally.

36. The method of claim 34 or 35, wherein step b) comprises hybridizing to said nucleic acid sample labeled oligonucleotide probes unique to wild-type and mutant IPF-1 sequences under conditions that permit specific hybridization of each probe to its target sequence.

37. The method of claim 34 or 35, wherein step b) comprises the steps of:
   i) amplifying by PCR a region of said IPF-1 gene to make amplified products that encompass said mutation,
   ii) cloning the products of said PCR of step i), and
   iii) performing DNA sequence analysis on multiple, independent clones resulting from said cloning of step ii) to detect the presence or absence of a mutation in each such clone, wherein detection of more than one sequence from among the clones resulting from a given sample is indicative of heterozygosity.

38. The method of claim 34 or 35, wherein step b) comprises the steps of:
   i) amplifying by PCR a region of said IPF-1 gene to make amplified products that encompass said mutation, and
   ii) performing SSCP on said amplified products, wherein observation of two conformers is indicative of heterozygosity.

39. A method for screening for pancreatic disease in a patient, comprising detecting an IPF-1 gene comprising the mutation IPF1ΔC, and wherein detection of said mutation is indicative of pancreatic disease.

40. The method of claim 39, wherein if said patient is homozygous for said mutation, said mutation is indicative of pancreatic agenesis.

41. The method of claim 39, wherein if said patient is heterozygous for said mutation, said mutation is indicative of the presence of diabetes mellitus.

42. The method of claim 41, wherein said diabetes mellitus is of the form early onset type II.

43. The method of claim 42, wherein said diabetes mellitus of the form early onset type II is MODY.

44. A method for screening a patient for pancreatic disease, comprising the steps:
   a) providing a nucleic acid sample from said patient, and
   b) detecting an IPF-1 gene comprising the mutation IPF1ΔC in said sample of step a), and wherein detection of said mutation is indicative of pancreatic disease.

45. The method of claim 44, wherein said patient is asymptomatic with regard to pancreatic disease.

46. The method of claim 44, wherein said patient is afflicted with symptoms of pancreatic disease.

47. The method of claim 46, wherein said patient is afflicted with symptoms of diabetes mellitus.

48. The method of claim 47, wherein said patient is afflicted with symptoms of diabetes mellitus of the form early onset type II.

49. The method of claim 48, wherein said patient is afflicted with symptoms of MODY.

50. The method of claim 44, wherein said nucleic acid sample is genomic DNA.

51. The method of claim 50, comprising a further step after step a) wherein a PCR product of the IPF-1 gene of said genomic DNA is generated for use in the detection of step b).

52. The method of claim 44, wherein said nucleic acid sample is mRNA.

53. The method of claim 52, further comprising the steps after said step a) wherein
   i) a reverse transcript of said mRNA is generated, and
   ii) a PCR product of the IPF-1 gene is made from said reverse transcript for use in the detection of step b).

54. The method of claim 50, 51, 52, or 53, wherein the detection of said mutation in the IPF-1 gene is performed by nucleic acid sequence analysis.

55. The method of claim 51 or 53, wherein the detection of said mutation in the IPF-1 gene is performed by SSCP.

56. A method for screening a plurality of patients for pancreatic disease, comprising the steps:
   a) providing a plurality of nucleic acid samples from a corresponding plurality of patients, and
   b) detecting an IPF-1 gene comprising the mutation IPF1ΔC in said plurality of samples of step a), and wherein detection of said mutation in a sample of said plurality of samples is indicative of pancreatic disease in a patient of said plurality of patients.

57. The method of claim 56, wherein said nucleic acid is genomic DNA.

58. The method of claim 57, wherein said plurality of patients comprises a group of unrelated individuals.

59. The method of claim 57, wherein said plurality of patients comprises a group of related individuals.

60. The method of claim 58 or 59 wherein said mutation is detected in said IPF-1 gene in a patient selected from said plurality of patients who is asymptomatic with regard to pancreatic disease.

61. The method of claim 60, wherein said pancreatic disease is diabetes mellitus.

62. The method of claim 61, wherein said diabetes mellitus is of the form early onset type II.

63. The method of claim 62, wherein said diabetes mellitus of the form early onset type II is MODY.

64. The method of claim 63, wherein said MODY is of the type MODY4.

65. The method of claim 59, in which a patient selected from said plurality of patients shows observable clinical manifestations of pancreatic disease.

66. The method of claim 65, in which said patient selected from said plurality of patients shows observable clinical manifestations of diabetes mellitus.

67. The method of claim 66, in which said patient selected from said plurality of patients shows observable clinical manifestations of diabetes mellitus of the form early onset type II.

68. The method of claim 67, in which said patient selected from said plurality of patients shows observable clinical manifestations of MODY.

69. The method of claim 68, in which said patient selected from said plurality of patients who shows observable clinical manifestations of MODY has MODY4.

70. A method of testing a patient who is afflicted with MODY to determine whether or not said patient has MODY4, comprising detecting an IPF-1 gene comprising the mutation IPF1ΔC, and wherein detection of said mutation is indicative of MODY4.

71. A method of screening for pancreatic disease in a patient whose parents both carry an inactivating mutation in the gene encoding IPF-1, comprising detecting an IPF-1 gene comprising the mutation IPF1ΔC, and wherein detection of said mutation is indicative of pancreatic disease.

72. The method of claim 71, wherein if said patient is heterozygous for said mutation, said mutation is indicative of MODY4.

73. The method of claim 71, wherein if said patient is homozygous for said mutation, said mutation is indicative of pancreatic agenesis.

74. The method of claim 72 or 73, wherein said screening is prenatal.

75. The method of claim 72 or 73, wherein said screening is postnatal.

76. A method for testing a patient for pancreatic agenesis or MODY4, comprising the steps:

a) providing a nucleic acid sample from said patient, b) performing on both allelic copies of the gene encoding IPF-1 a detection step for an IPF-1 gene comprising the mutation IPF1ΔC, and c) detecting said mutation in one or both of said allelic copies of said gene in said sample, wherein homozygosity of said mutation is indicative of pancreatic agenesis and wherein heterozygosity of said mutation is indicative of MODY4.

77. The method of claim 76, wherein said testing is performed prenatally.

78. The method of claim 76, wherein said testing is performed postnatally.

79. The method of claim 77 or 78, wherein steps b) and c) comprise the steps of:

i) hybridizing to said nucleic acid sample equimolar amounts of labeled oligonucleotide probes unique for wild-type and mutant IPF-1 sequences under conditions that permit specific hybridization of each probe to its target sequence, and ii) comparing quantitatively the extent of hybridization of the two probes to molecules present in said nucleic acid sample, wherein non-hybridization of the wild-type probe indicates homozygosity for the mutant allele and non-hybridization of the mutant probe indicates homozygosity for the wild-type allele, and wherein a 1:1 ratio of hybridization of wild-type and mutant probes indicates heterozygosity for the two alleles.

80. The method of claim 77 or 78, wherein steps b) and c) comprise the steps of:

i) amplifying by PCR a region of said IPF-1 gene to make amplified products that encompass said mutation, ii) cloning the products of said PCR of step i), and iii) performing DNA sequence analysis on multiple, independent clones resulting from said cloning of step ii) to detect the presence or absence of a mutation in each such clone, wherein the failure to detect more than one sequence from among the clones resulting from a given sample is indicative of homozygosity.

81. The method of claim 77 or 78, wherein steps b) and c) comprise the steps of:

i) amplifying by PCR a region of said IPF-1 gene to make amplified products that encompass said mutation, and ii) performing SSCP on said amplified products, wherein observation of one conformer is indicative of homozygosity and wherein observation of two conformers is indicative of heterozygosity.

82. An isolated nucleic acid comprising the nucleotide sequence of SEQ ID NO: 1, with the exception that any one of nucleotides 202–207 is deleted, wherein said nucleic acid encodes a truncated IPF-1 protein.

* * * * *